(12) United States Patent
Cozma et al.

(10) Patent No.: US 11,097,016 B2
(45) Date of Patent: Aug. 24, 2021

(54) USE OF LYSO-GB1 AS DRUGGABLE TARGET

(71) Applicant: Centogene GmbH, Rostock (DE)

(72) Inventors: Claudia Cozma, Rostock (DE); Peter Bauer, Tubingen (DE)

(73) Assignee: Centogene GmbH, Rostock (DE)

( * ) Notice: Subject to any disclaimer, the term of this patent is extended or adjusted under 35 U.S.C. 154(b) by 0 days.

(21) Appl. No.: 16/312,090

(22) PCT Filed: Jul. 3, 2017

(86) PCT No.: PCT/EP2017/000786
§ 371 (c)(1),
(2) Date: Dec. 20, 2018

(87) PCT Pub. No.: WO2018/001565
PCT Pub. Date: Jan. 4, 2018

(65) Prior Publication Data
US 2019/0201554 A1 Jul. 4, 2019

(30) Foreign Application Priority Data
Jul. 1, 2016 (EP) .................................... 16001474

(51) Int. Cl.
| | | |
|---|---|---|
| C12Q 1/00 | (2006.01) | |
| G01N 33/53 | (2006.01) | |
| A61K 49/00 | (2006.01) | |
| G01N 33/68 | (2006.01) | |
| G01N 33/50 | (2006.01) | |

(52) U.S. Cl.
CPC ..... A61K 49/0008 (2013.01); G01N 33/6896 (2013.01); *G01N 33/5008* (2013.01); *G01N 33/5091* (2013.01); *G01N 2800/085* (2013.01); *G01N 2800/28* (2013.01); *G01N 2800/2835* (2013.01); *G01N 2800/38* (2013.01); *G01N 2800/385* (2013.01)

(58) Field of Classification Search
CPC ........... G01N 33/5008; G01N 33/5091; G01N 2800/085
See application file for complete search history.

(56) References Cited

FOREIGN PATENT DOCUMENTS

| WO | WO 2012/094600 A1 | 7/2012 |
|---|---|---|
| WO | WO 2015/119989 A1 | 8/2015 |

OTHER PUBLICATIONS

U. H Schueler et al., „ Toxisity of glucosylsphingosine (glucopsychosine) to cultured neuronal cells: a model system for assessing neuronal damage in Gaucher disease type 2 and 3, Neurobiology of Disease, vol. 14, No. 3, pp. 595-601, Dec. 1, 2003 (Dec. 1, 2003).

John Flanagan et al:, „ The origins of gluposylsphingosine in Gaucher disease, Molecular and Metabolism, vol. 108, No. 2, pp. S40-S41, Feb. 1, 2013 (Feb. 1, 2013).
Cabrera-Salazar et al., "Intracerebroventricular delivery of glucocerebrosidase reduces substrates and increases lifespan in a mouse model of neuronopathic Gaucher disease," *Experimental Neurology*, 2010, vol. 225, pp. 436-444.
Cabrera-Salazar et al., "Systemic Delivery of a Glucosylceramide Synthase Inhibitor Reduces CNS Substrates and Increases Lifespan in a Mouse Model of Type 2 Gaucher Disease," *PLOS ONE*, Aug. 2012, vol. 7, Issue 8, pp. 1-9.
Cox et al., "The role of the iminosugar N-butyldeoxynojirimycin (miglustat) in the management of type I (non-neuronopathic) Gaucher disease: A position statement," *J. Inherit. Metab. Dis.*, 2003, vol. 26, pp. 513-526.
Dekker et al., "Elevated plasma glucosylsphingosine in Gaucher disease: relation to phenotype, storage cell markers, and therapeutic response," *Blood*, Oct. 20, 2011, vol. 118, No. 16, pp. e118-e127.
Farfel-Becker et al., "Animal models for Gaucher disease research," *Disease Models & Mechanisms*, 2011, vol. 4, pp. 746-752.
Grabowski et al., "Dose-response relationships for enzyme replacement therapy with imiglucerase/alglucerase in patients with Gaucher disease type 1," *Genetics*, Feb. 2009, vol. 11, No. 2, pp. 92-100.
International Search Report and Written Opinion, PCT/EP2017/000786, dated Nov. 21, 2017, 24 pages.
Marshall et al., "CNS-accessible Inhibitor of Glucosylceramide Synthase for Substrate Reduction Therapy of Neuronopathic Gaucher Disease," *Molecular Therapy*, Jun. 2016, vol. 24, No. 6, pp. 1019-1029.
Mizukami et al., "Systemic inflammation in glucocerebrosidase-deficient mice with minimal glucosylceramide storage," *The Journal of Clinical Investigation*, May 2002, vol. 109, No. 9, pp. 1215-1221.
Orvisky et al., "Glucosylsphingosine Accumulation in Mice and Patients with Type 2 Gaucher Disease Begins Early in Gestation," *Pediatric Research*, 2000, vol. 48, No. 2, pp. 233-237.
Rolfs et al., "Glucosylsphingosine is a Highly Sensitive and Specific Biomarker for Primary Diagnostic and Follow-Up Monitoring in Gaucher Disease in a Non-Jewish, Caucasian Cohort of Gaucher Disease Patients," *PLOS ONE*, Nov. 2013, vol. 8, Issue 11, pp. 1-9.
Weinreb et al., "Effectiveness of Enzyme Replacement Therapy in 1028 Patients with Type 1 Gaucher Disease after 2 to 5 Years of Treatment: A Report from the Gaucher Registry," *The American Journal of Medicine*, Aug. 1, 2002, vol. 113, pp. 112-119.

*Primary Examiner* — Shin Lin Chen
(74) *Attorney, Agent, or Firm* — Stanek Lemon Crouse & Meeks, PA

(57) ABSTRACT

The present invention is related to the in vitro use of lyso-Gb1 as a draggable target in the development of a drug, and to antagonist of lyso-Gb1 for use in the treatment and/or prevention of a disease, wherein the disease is Gaucher disease or Parkinson's disease.

4 Claims, 10 Drawing Sheets

Table 1A

| Median (IQR) | body weight on day of analysis g | AST (GOT) U/l | Leuko- G/l | Erythro- T/l | Hb g/dl | PCV % | MCV fl | MCH pg | MCHC g/dl | Thrombo- G/l | relative g/100g b.w. | relative spleen weight g/kg b.w. |
|---|---|---|---|---|---|---|---|---|---|---|---|---|
| baseline | 25.6 (1.2) | 66.0 (42.0) | 6.4 (2.3) | 8.6 (1.0) | 12.9 (.4) | 39.0 (.8) | 45.0 (2.3) | 14.9 (.2) | 33.0 (.8) | 869.5 (431.3) | n.d. | n.d. |
| 4 wk vehicle | 28.7 (2.5) | 56.0 (23.5) | 7.7 (2.7) | 9.0 (.8) | 13.2 (.9) | 40.5 (1.0) | 45.5 (3.3) | 14.9 (.7) | 32.0 (1.5) | 896.0 (217.3) | n.d. | n.d. |
| 4 wk lysogb1 | 27.3 (1.4) | 47.0 (25.0) | 8.2 (2.4) | 8.5 (.5) | 12.3 (.5) | 37.5 (1.8) | 44.0 (2.3) | 14.4 (.5) | 33.0 (1.0) | 1046.0 (280.5) | n.d. | n.d. |
| 8 wk vehicle | 30.2 (1.6) | 43.5 (15.8) | 9.6 (3.9) | 9.3 (.8) | 13.5 (.9) | 41.5 (4.0) | 44.0 (.8) | 14.6 (.6) | 33.0 (.8) | 1065.0 (208.5) | 4.8 (.5) | 2.5 (.2) |
| 8 wk lysogb1 | 29.7 (3.5) | 55.5 (16.3) | 8.4 (3.9) | 8.6 (.7) | 12.4 (.8) | 37.5 (2.8) | 43.5 (2.3) | 14.7 (.3) | 33.0 (1.3) | 1226.0 (207.5) | 5.3 (.3) | 3.3 (1.0) |
| 12 wk vehicle | 32.7 (3.9) | 68.0 (16.5) | 4.8 (3.4) | 8.6 (.2) | 12.7 (.2) | 37.0 (.0) | 44.0 (.8) | 15.0 (.4) | 35.0 (.8) | 1268.0 (395.5) | 5.0 (.7) | 2.4 (.2) |
| 12 wk lysogb1 | 32.5 (3.2) | 75.0 (32.0) | 5.8 (2.4) | 8.3 (.4) | 12.2 (.3) | 36.0 (.5) | 43.0 (.5) | 14.6 (.8) | 34.0 (.3) | 1157.0 (364.5) | 5.2 (.3) | 2.9 (.6) |

TABLE 1B

| Median | GM-CSF pg/ml | IFN-gamma pg/ml | IL-1 beta pg/ml | IL-10 pg/ml | IL-12p70 pg/ml | IL-13 pg/ml | IL-17A pg/ml | IL-18 pg/ml | IL-2 pg/ml | IL-22 pg/ml | IL-23 pg/ml | IL-27 pg/ml | IL-4 pg/ml | IL-5 pg/ml | IL-6 pg/ml | IL-9 pg/ml | TNF-alpha pg/ml |
|---|---|---|---|---|---|---|---|---|---|---|---|---|---|---|---|---|---|
| baseline | 0,00 | 0,85 | 0,46 | 0,00 | 0,83 | 0,00 | 7,14 | 109,82 | 1,30 | 37,73 | 9,28 | 9,66 | 1,35 | 6,15 | 0,59 | 0,00 | 0,00 |
| 4wk vehicle | 0,00 | 0,27 | 0,23 | 0,00 | 0,45 | 0,00 | 3,43 | 100,23 | 0,00 | 10,23 | 4,78 | 5,78 | 0,81 | 5,25 | 3,31 | 0,00 | 0,00 |
| 4 wk lysogb1 | 4,41 | 0,85 | 0,46 | 0,00 | 1,21 | 0,45 | 4,22 | 136,52 | 1,30 | 24,71 | 5,40 | 6,56 | 1,42 | 7,02 | 16,85 | 0,00 | 2,58 |
| 8 wk vehicle | 3,33 | 1,22 | 0,74 | 0,00 | 0,95 | 0,31 | 2,99 | 167,84 | 4,22 | 33,52 | 5,40 | 8,87 | 1,56 | 7,88 | 5,90 | 0,00 | 2,33 |
| 8 wk lysogb1 | 4,41 | 1,23 | 1,03 | 0,00 | 1,21 | 0,62 | 5,28 | 167,84 | 10,09 | 37,73 | 6,74 | 9,65 | 1,42 | 6,15 | 16,64 | 0,00 | 2,45 |
| 12 wk vehicle | 3,33 | 0,66 | 0,07 | 0,00 | 0,95 | 0,15 | 2,64 | 142,83 | 0,00 | 24,33 | 4,01 | 9,66 | 1,57 | 4,78 | 7,06 | 0,00 | 0,08 |
| 12 wk lysogb1 | 5,20 | 1,41 | 1,29 | 0,00 | 1,34 | 0,31 | 4,95 | 173,61 | 0,00 | 24,91 | 20,63 | 9,27 | 2,08 | 7,02 | 20,71 | 0,00 | 1,20 |

Fig. 6

USE OF LYSO-GB1 AS DRUGGABLE TARGET

CROSS-REFERENCE TO RELATED APPLICATIONS

This application is a 35 U.S.C. § 371 National Stage Entry of International Application No. PCT/EP2017/000786 having an international filing date of Jul. 3, 2017, which claims the benefit of European Application No. EP 16 001 474.2 filed Jul. 1, 2016, the contents of which are hereby incorporated herein by reference in their entireties.

The present invention is related to the use of lyso-Gb1, an antagonist of lyso-Gb1, use of an antagonist of lyso-Gb1, a method for the generation of an animal model for a disease, a method for the screening of an agent suitable for and/or capable of treating and/or preventing a disease, and a method for the assessment of the effects of an agent in the treatment and/or prevention of a disease.

Modern drug development no longer relies on a more or less heuristic approach, but typically involves the elucidation of the molecular mechanism underlying a disease or a condition, the identification of candidate target molecules and the evaluation of said target molecules. Once such a validated target molecule, which is herein referred to also as target, is available, drug candidates directed thereto may be tested. In many cases such drug candidates are members of a compound library which may consist of synthetic or natural compounds. Also the use of combinatorial libraries is common. Such compound libraries are herein also referred to as candidate compound libraries. Although in the past this approach has proven to be successful, it is still time and money consuming. Different technologies are currently applied for target identification and target validation.

A further prerequisite for drug development is the availability of an animal model for a disease or condition in question. The absence of an appropriate animal model increases the risk of failure of any drug development as there is a considerable gap between cell-based assays used in the screening, characterization and assessment of drug candidates and the testing of such drug candidates in a human body, with the results obtained in cell-based assays typically not allowing a comprehensive and fact-based prediction as to the behaviour of a drug candidate in a human body. However, also the quality of an animal model for a disease and condition, respectively, in question is important. The better the animal model reflects the particularities of the disease and disorder, respectively, in question in man, the more reliable are the results obtained from the testing of a drug candidate which significantly reduces the risk that a drug candidate ultimately fails in the treatment of a human patient.

Among the plethora of human diseases, lysosomal storage diseases, also referred to herein as lysosomal storage disorders or LSDs, are a group of rare inherited metabolic disorders that result from defects in lysosomal function. LSDs result when a specific organelle in the body's cells—the lysosome—malfunctions. Some of the more prominent lysosomal storage diseases are Gaucher's disease and Fabry disease.

LSDs are caused by lysosomal dysfunction usually as a consequence of deficiency of a single enzyme required for the metabolism of lipids, glycoproteins or so-called mucopolysaccharides. Individually, LSDs occur with frequencies of about 1:10,000 to 1:250,000, however, as a group the incidence is about 1:5,000. Most of these disorders are autosomal recessively inherited; however, a few are X-linked inherited, such as Fabry disease and Hunter syndrome.

Like other genetic diseases, individuals typically inherit lysosomal storage diseases from their parents. Although each disorder results from different gene mutations that translate into a deficiency in enzyme activity, they all share a common biochemical characteristic—nearly all lysosomal disorders originate from an abnormal accumulation of substances inside the lysosome.

Lysosomal storage diseases affect mostly children and they often die at young and unpredictable age, many within a few months or years of birth. Many other children die of this disease following years of suffering from various symptoms of their particular disorder.

The symptoms of lysosomal storage disease vary, depending on the particular disorder and other variables like the age of onset, and can be mild to severe. They can include developmental delay, movement disorders, seizures, dementia, deafness and/or blindness. Some people with lysosomal storage disease have enlarged livers (hepatomegaly) and enlarged spleens (splenomegaly), pulmonary and cardiac problems, and bones that develop abnormally.

So far, there are no causative cures for lysosomal storage diseases and treatment is mostly symptomatic, although bone marrow transplantation and enzyme replacement therapy (abbr. ERT) have been used for some indications with good success. In addition, umbilical cord blood transplantation is being performed at specialized centers for a number of these diseases. In addition, substrate reduction therapy (abbr. SRT), a method used to decrease the accumulation of storage material, is currently being evaluated for some of these diseases. Furthermore, chaperone therapy, a technique used to stabilize the defective enzymes produced by patients, is being examined for certain of these disorders. Gene therapy constitutes a further option for the treatment of these diseases.

One prominent disease from the group of lysosomal storage diseases is Gaucher disease. Gaucher disease is caused by a genetic defect of the glucocerebrosidase gene (abbr. GBA gene) resulting in a deficiency of the corresponding lysosomal enzyme glucocerebrosidase (abbr. GCase). The developing discrepancy of glucosylceramide (abbr. GlcCer) build-up in the Endoplasmic Reticulum and degradation in the lysosomes of the cells leads to prominent accumulation of GlcCer in tissue macrophages. Among the major clinical symptoms of Gaucher disease are liver and spleen enlargement, decreased red blood cells and thrombocytes and skeletal abnormalities causing an increased risk of fractures and osteonecrosis. Glucosylsphingosine (abbr. lyso-Gb1), the deacylated form of glucosylceramide, has recently been identified as a sensitive and specific biomarker for Gaucher disease (see, for example, international patent application WO 2012/167925).

The accumulation of the lyso-Gb in cerebrum and cerebellum in infantile and juvenile GD patients has firstly been documented in 1982 (Nilsson et al., 1982, J Neurochem 39: 709-718). Lyso-Gb1 is an amphipathic compound that has been reported to originate from the enzymatic action of lysosomal acid ceramidase on the cell's primary glycosphingolipid storage product, glucosylceramide (Flanagan et al., 2013, Mol Genet Metab 108:S40-41; Ferraz et al., 2016, FEBS Lett 590:716-725). Lyso-Gb1 is highly abundant in the brain tissue of patients with neuronopathic GD, but not in non-neuronopathic GD patients (Orvisky et al, 2002, Mol Genet Metab 76: 262-70).

A problem underlying the present invention was the provision of a target which is suitable for therapeutic approaches in the treatment of a lysosomal storage disorder and Gaucher disease in particular.

A problem underlying the present invention was the provision of a target which is suitable for therapeutic approaches in the treatment of Parkinson's disease.

Another problem underlying the present invention was the provision of an animal model, more particularly an animal model for a lysosomal storage disorder and Gaucher disease in particular, and means for the generation of such animal model.

Another problem underlying the present invention was the provision of an animal model, more particularly an animal model for Parkinson's disease, and means for the generation of such animal model.

A further problem underlying the present invention was the provision of means for the treatment and/or prevention of a disease, preferably a lysosomal storage disorder and more preferably Gaucher disease.

A further problem underlying the present invention was the provision of means for the treatment and/or prevention of a disease, preferably Parkinson's disease.

A still further problem underlying the present invention was the provision of a method for the screening of an agent suitable for and/or capable of treating and/or preventing a disease, whereby by disease is preferably a lysosomal storage disorder and more preferably Gaucher disease.

A still further problem underlying the present invention was the provision of a method for the screening of an agent suitable for and/or capable of treating and/or preventing a disease, whereby by disease is Parkinson's disease.

Finally, a problem underlying the present invention was the provision of a method for the assessment of the effects of an agent in the treatment and/or prevention of a disease, whereby the disease is preferably a lysosomal storage disorder and more preferably Gaucher disease.

Similarly, a problem underlying the present invention was the provision of a method for the assessment of the effects of an agent in the treatment and/or prevention of a disease, whereby the disease is Parkinson's disease.

These and other problems underlying the present invention are solved by the subject matter of the attached claims. Additionally, these and other problems underlying the present invention are solved by the subject matter of the following embodiments.

EMBODIMENT 1

Use of lyso-Gb1 as a target in the treatment of a disease.

EMBODIMENT 2

Use of lyso-Gb1 according to embodiment 1, wherein the disease is a lysosomal storage disorder (LSD).

EMBODIMENT 3

Use according to any one of embodiments 1 to 2, wherein the lysosomal storage disorder is a lysosomal storage disorder caused by a defective activity of glucocerebrosidase.

EMBODIMENT 4

Use according to any one of embodiments 1 to 3, wherein the disease is Gaucher disease.

EMBODIMENT 5

Use according to embodiment 4, wherein Gaucher disease is a mild form of Gaucher disease.

EMBODIMENT 6

Use according to embodiment 4, wherein Gaucher disease is non-neuronopathic Gaucher disease.

EMBODIMENT 7

Use according to embodiment 4, wherein Gaucher disease is a neuronopathic Gaucher disease.

EMBODIMENT 8

Use according to any one of embodiments 1 to 4, wherein the disease is selected from the group comprising type 1 Gaucher disease, type 2 Gaucher disease and type 3 Gaucher disease.

EMBODIMENT 9

Use according to embodiment 8, wherein the disease is type 1 Gaucher disease.

EMBODIMENT 10

Use according to any one of embodiments 1 to 8, wherein the disease is type 2 Gaucher disease or type 3 Gaucher disease.

EMBODIMENT 11

Use according to embodiment 1, wherein the disease is Parkinson's disease.

EMBODIMENT 12

Use according to any one of embodiments 1 to 11, wherein the target is a druggable target.

EMBODIMENT 13

Use according to any one of embodiments 1 to 12, wherein the target is an in vitro target.

EMBODIMENT 14

Use according to any one of embodiments 1 to 13, wherein the use is an in vitro use.

EMBODIMENT 15

Use according to any one of embodiments 1 to 12, wherein the target is an in vivo target.

EMBODIMENT 16

Use according to any one of embodiments 1 to 12 and 15, wherein the use is an in vivo use.

EMBODIMENT 17

Use of lyso-Gb1 as a target in the development of a drug, preferably the drug is capable of and/or suitable for treating and/or preventing a disease

EMBODIMENT 18

Use of lyso-Gb1 according to embodiment 17, wherein the disease is a lysosomal storage disorder (LSD).

EMBODIMENT 19

Use according to any one of embodiments 17 to 18, wherein the lysosomal storage disorder is a lysosomal storage disorder caused by a defective activity of glucocerebrosidase.

EMBODIMENT 20

Use according to any one of embodiments 17 to 19, wherein the disease is Gaucher disease.

EMBODIMENT 21

Use according to embodiment 20, wherein Gaucher disease is a mild form of Gaucher disease.

EMBODIMENT 22

Use according to any one of embodiments 20 to 21, wherein Gaucher disease is non-neuronopathic Gaucher disease.

EMBODIMENT 23

Use according to embodiment 20, wherein Gaucher disease is a neuronopathic Gaucher disease.

EMBODIMENT 24

Use according to any one of embodiments 17 to 21, wherein the disease is selected from the group comprising type 1 Gaucher disease, type 2 Gaucher disease and type 3 Gaucher disease.

EMBODIMENT 25

Use according to embodiment 24, wherein the disease is type 1 Gaucher disease.

EMBODIMENT 26

Use according to any one of embodiments 17 to 24, wherein the disease is type 2 Gaucher disease or type 3 Gaucher disease.

EMBODIMENT 27

Use according to embodiment 17, wherein the disease is Parkinson's disease.

EMBODIMENT 28

Use according to any one of embodiments 17 to 27, wherein the target is a druggable target.

EMBODIMENT 29

Use according to any one of embodiments 17 to 28, wherein the drug is an antagonist of lyso-Gb1.

EMBODIMENT 30

Use according to embodiment 29, wherein the antagonist is capable of reducing or ameliorating at least one symptom of a disease.

EMBODIMENT 31

Use according to embodiment 29, wherein the antagonist is capable of treating a disease, preferably in humans.

EMBODIMENT 32

Use according to embodiment 29, wherein the antagonist is capable of reducing or ameliorating at least one symptom of a disease in an animal model of the disease.

EMBODIMENT 33

Use according to embodiment 29, wherein antagonist is capable of treating a disease in an animal model of the disease.

EMBODIMENT 34

Use according to any one of embodiments 29 to 33, wherein the disease is any disease as defined in any one of embodiments 18 to 27.

EMBODIMENT 35

Use according to any one of embodiments 32 to 34, wherein the animal model is a lyso-Gb1 induced animal model.

EMBODIMENT 36

Use according to any one of embodiments 32 to 35, wherein the animal model is an animal model for the disease.

EMBODIMENT 37

Use according to embodiment 36, wherein the animal model for or of the disease is an animal model for a disease as defined in any one of embodiments 18 to 27.

EMBODIMENT 38

Use according to any one of embodiments 32 to 37, wherein the animal model is a mammal.

EMBODIMENT 39

Use according to embodiment 38, wherein the mammal is a rodent.

EMBODIMENT 40

Use according to embodiment 39, wherein the rodent is selected from the group comprising mouse and rat.

EMBODIMENT 41

Use according to embodiment 38, wherein the mammal is selected from the group comprising a primate, a dog, a pig and a sheep.

EMBODIMENT 42

Use according to any one of embodiments 29 to 41, wherein the antagonist is capable of reducing at least one peripheral symptom of the disease.

EMBODIMENT 43

Use according to embodiment 42, wherein the at least one peripheral symptom of the disease is selected from the group comprising visceral enlargement of the spleen, mild anemia and inflammatory tissue response, preferably at least one peripheral symptom of type 1, of type 2 and/or of type 3 Gaucher disease, more preferably of type 1 Gaucher disease.

EMBODIMENT 44

Use according to embodiment 43, wherein the animal model is a mouse animal model.

EMBODIMENT 45

Use according to embodiment 44, wherein the mouse animal model is a lyso-Gb1 induced animal mouse model.

EMBODIMENT 46

Use according to embodiment 45, wherein the lyso-Gb1 induced animal mouse model is a lyso-Gb1 induced model for Gaucher disease, preferably the mouse is selected from the group comprising a C57BL/6JRj mouse, a C57BL/6 mouse and a C57/BL/10 mouse.

EMBODIMENT 47

Use according to embodiment 46, wherein Gaucher disease is selected from the group comprising mild form of Gaucher disease, type 1 Gaucher disease and non-neuronopathic Gaucher disease.

EMBODIMENT 48

Use according to any one of embodiments 17 to 47, wherein the drug is selected from the group comprising a small molecule, a lyso-Gb1 binding protein, a lyso-Gb1 binding peptide, an antibody or antigen-binding fragment thereof, an anticalin, an aptamer, a spiegelmer, and a lyso-Gb1 degrading enzyme.

EMBODIMENT 49

Use according to embodiment 48, wherein the antibody is an anti-lyso-Gb1 antibody and the antibody fragment is a lyso-Gb1 binding fragment of the antibody.

EMBODIMENT 50

Use according to embodiment 48, wherein the aptamer, the spiegelmer and the anticalin is each binding to or capable of binding to lyso-Gb1.

EMBODIMENT 51

Use of lyso-Gb1 in the generation of an animal model of a disease.

EMBODIMENT 52

Use of lyso-Gb1 according to embodiment 51, wherein the disease is a lysosomal storage disorder (LSD).

EMBODIMENT 53

Use according to any one of embodiments 51 to 52, wherein the lysosomal storage disorder is a lysosomal storage disorder caused by a defective activity of glucocerebrosidase.

EMBODIMENT 54

Use according to any one of embodiments 51 to 53, wherein the disease is Gaucher disease.

EMBODIMENT 55

Use according to embodiment 54, wherein Gaucher disease is a mild form of Gaucher disease.

EMBODIMENT 56

Use according to embodiment 55, wherein Gaucher disease is non-neuronopathic Gaucher disease.

EMBODIMENT 57

Use according to embodiment 54, wherein Gaucher disease is a neuronopathic Gaucher disease.

EMBODIMENT 58

Use according to any one of embodiments 51 to 55, wherein the disease is selected from the group comprising type 1 Gaucher disease, type 2 Gaucher disease and type 3 Gaucher disease.

EMBODIMENT 59

Use according to embodiment 58, wherein the disease is type 1 Gaucher disease.

EMBODIMENT 60

Use according to any one of embodiments 51 to 58, wherein the disease is type 2 Gaucher disease or type 3 Gaucher disease.

EMBODIMENT 61

Use according to any one of embodiments 51 to 58, wherein the disease is type 3 Gaucher disease.

EMBODIMENT 62

Use according to embodiment 51, wherein the disease is Parkinson's disease.

EMBODIMENT 63

Use according to any one of embodiments 51 to 62, wherein the animal model is a lyso-Gb1 induced animal model.

EMBODIMENT 64

Use according to any one of embodiments 51 to 63, wherein the animal model is a mammal.

EMBODIMENT 65

Use according to embodiment 64, wherein the mammal is a rodent.

EMBODIMENT 66

Use according to embodiment 65, wherein the rodent is selected from the group comprising mouse and rat.

EMBODIMENT 67

Use according to embodiment 64, wherein the mammal is selected from the group comprising a primate, a dog, a pig and a sheep.

EMBODIMENT 68

Use according to embodiment 66, wherein the animal model is a mouse animal model.

EMBODIMENT 69

Use according to embodiment 68, wherein the mouse animal model is a lyso-Gb1 induced mouse animal model.

EMBODIMENT 70

Use according to embodiment 69, wherein the lyso-Gb1 induced mouse model is a lyso-Gb1 induced mouse model for Gaucher disease, preferably the mouse is selected from the group comprising a C57BL/6JRj mouse, a C57BL/6 mouse and a C57/BL/10 mouse.

EMBODIMENT 71

Use according to embodiment 70, wherein Gaucher disease is selected from the group comprising mild form of Gaucher disease, type 1 Gaucher disease and non-neuronopathic Gaucher disease.

EMBODIMENT 72

An antagonist of lyso-Gb1 for use in the treatment and/or prevention of a disease.

EMBODIMENT 73

The antagonist for use according to embodiment 72, wherein the antagonist is selected from the group comprising a small molecule, a lyso-Gb1 binding protein, a lyso-Gb1 binding peptide, an antibody or antigen-binding fragment thereof, an anticalin, an aptamer, a spiegelmer, and a lyso-Gb1 degrading enzyme.

EMBODIMENT 74

The antagonist for use according to embodiment 73, wherein the antibody is an anti-lyso-Gb1 antibody and the antibody fragment is a lyso-Gb1 binding fragment of the antibody.

EMBODIMENT 75

The antagonist for use according to embodiment 73, wherein the aptamer and the spiegelmer is each binding to or capable of binding to lyso-Gb1.

EMBODIMENT 76

The antagonist for use according to any one of embodiments 72 to 75, wherein the disease is a lysosomal storage disorder (LSD).

EMBODIMENT 77

The antagonist for use according to embodiment 76, wherein the lysosomal storage disorder is a lysosomal storage disorder caused by a defective activity of glucocerebrosidase.

EMBODIMENT 78

The antagonist for use according to any one of embodiments 72 to 77, wherein the disease is Gaucher disease, preferably the antagonist is capable of reducing at least one peripheral symptom of the Gaucher disease, wherein more preferably the at least one peripheral symptom of the disease is selected from the group comprising visceral enlargement of the spleen, mild anemia and inflammatory tissue response, preferably at least one peripheral symptom of type 1, of type 2 and/or of type 3 Gaucher disease, more preferably of type 1 Gaucher disease.

EMBODIMENT 79

The antagonist for use according to embodiment 78, wherein Gaucher disease is a mild form of Gaucher disease.

EMBODIMENT 80

The antagonist for use according to embodiment 78, wherein Gaucher disease is non-neuronopathic Gaucher disease.

EMBODIMENT 81

The antagonist for use according to embodiment 78, wherein Gaucher disease is a neuronopathic Gaucher disease.

EMBODIMENT 82

The antagonist for use according to any one of embodiments 72 to 78, wherein the disease is selected from the group comprising type 1 Gaucher disease, type 2 Gaucher disease and type 3 Gaucher disease.

EMBODIMENT 83

The antagonist for use according to embodiment 82, wherein the disease is type 1 Gaucher disease.

EMBODIMENT 84

The antagonist for use according to any one of embodiments 72 to 82, wherein the disease is type 2 Gaucher disease or type 3 Gaucher disease.

EMBODIMENT 85

The antagonist for use according to embodiment 72, wherein the disease is Parkinson's disease.

EMBODIMENT 86

Use of an antagonist of lyso-Gb1 in the manufacture of a medicament.

EMBODIMENT 87

Use according to embodiment 86, wherein the antagonist is selected from the group comprising a small molecule, a lyso-Gb1 binding protein, a lyso-Gb1 binding peptide, an antibody or antigen-binding fragment thereof, an anticalin, an aptamer, a spiegelmer, and a lyso-Gb1 degrading enzyme.

EMBODIMENT 88

Use according to embodiment 87, wherein the antibody is an anti-lyso-Gb1 antibody and the antibody fragment is a lyso-Gb1 binding fragment of the antibody.

EMBODIMENT 89

Use according to embodiment 87, wherein the aptamer, the spiegelmer and the anticalin is each binding to or capable of binding to lyso-Gb1.

EMBODIMENT 90

Use according to any one of embodiments 86 to 89, wherein the disease is a lysosomal storage disorder (LSD).

EMBODIMENT 91

Use according to embodiment 90, wherein the lysosomal storage disorder is a lysosomal storage disorder caused by a defective activity of glucocerebrosidase.

EMBODIMENT 92

Use according to any one of embodiments 86 to 91, wherein the disease is Gaucher disease, preferably the medicament is capable of reducing at least one peripheral symptom of Gaucher disease, wherein more preferably the at least one peripheral symptom of the disease is selected from the group comprising visceral enlargement of the spleen, mild anemia and inflammatory tissue response, more preferably at least one peripheral symptom of type 1 Gaucher disease, of type 2 and/or of type 3 Gaucher disease, most preferably of type 1 Gaucher disease.

EMBODIMENT 93

Use according to embodiment 91, wherein Gaucher disease is a mild form of Gaucher disease.

EMBODIMENT 94

Use according to embodiment 92, wherein Gaucher disease is non-neuronopathic Gaucher disease.

EMBODIMENT 95

Use according to embodiment 92, wherein Gaucher disease is a neuronopathic Gaucher disease.

EMBODIMENT 96

Use according to any one of embodiments 86 to 92, wherein the disease is selected from the group comprising type 1 Gaucher disease, type 2 Gaucher disease and type 3 Gaucher disease.

EMBODIMENT 97

Use according to embodiment 96, wherein the disease is type 1 Gaucher disease.

EMBODIMENT 98

Use according to any one of embodiments 86 to 96, wherein the disease is type 2 Gaucher disease or type 3 Gaucher disease.

EMBODIMENT 99

Use according to embodiment 86, wherein the disease is Parkinson's disease.

EMBODIMENT 100

A method for the generation of an animal model for a disease, wherein the method comprises
a) administering to an animal lyso-Gb1 over a period of time,
b) determining whether the animal shows at least one symptom of the disease.

EMBODIMENT 101

The method according to embodiment 100, wherein the disease is a lysosomal storage disorder (LSD).

EMBODIMENT 102

The method according to embodiment 101, wherein the lysosomal storage disorder is a lysosomal storage disorder caused by a defective activity of glucocerebrosidase.

EMBODIMENT 103

The method according to any one of embodiments 100 to 102, wherein the disease is Gaucher disease.

EMBODIMENT 104

The method according to embodiment 102, wherein Gaucher disease is a mild form of Gaucher disease.

EMBODIMENT 105

The method according to embodiment 103, wherein Gaucher disease is non-neuronopathic Gaucher disease.

EMBODIMENT 106

The method according to embodiment 103, wherein Gaucher disease is a neuronopathic Gaucher disease.

EMBODIMENT 107

The method according to any one of embodiments 100 to 103, wherein the disease is selected from the group comprising type 1 Gaucher disease, type 2 Gaucher disease and type 3 Gaucher disease.

EMBODIMENT 108

The method for use according to embodiment 107, wherein the disease is type 1 Gaucher disease.

EMBODIMENT 109

The method according to any one of embodiments 100 to 107, wherein the disease is type 2 Gaucher disease or type 3 Gaucher disease.

EMBODIMENT 110

The method according to embodiment 100, wherein the disease is Parkinson's disease.

EMBODIMENT 111

The method according to any one of embodiments 100 to 110, wherein the animal model is a lyso-Gb1 induced animal model.

EMBODIMENT 112

The method according to any one of embodiments 100 to 111, wherein the animal model is a mammal.

EMBODIMENT 113

The method according to embodiment 112, wherein the mammal is a rodent.

EMBODIMENT 114

The method according to embodiment 113, wherein the rodent is selected from the group comprising mouse and rat.

EMBODIMENT 115

The method according to embodiment 113, wherein the mammal is selected from the group comprising a primate, a dog, a pig and a sheep.

EMBODIMENT 116

The method according to embodiment 112, wherein the animal model is a mouse animal model.

EMBODIMENT 117

The method according to embodiment 116, wherein the mouse animal model is a lyso-Gb1 induced mouse animal model.

EMBODIMENT 118

The method according to embodiment 117, wherein the lyso-Gb1 induced mouse model is a lyso-Gb1 induced animal mouse model for Gaucher disease.

EMBODIMENT 119

The method according to embodiment 118, wherein Gaucher disease is selected from the group comprising mild form of Gaucher disease, type 1 Gaucher disease and non-neuronopathic Gaucher disease.

EMBODIMENT 120

The method according to any one of embodiments 100 to 119, wherein lyso-Gb1 is administered until the animal shows at least one symptom of the disease.

EMBODIMENT 121

The method according to any one of embodiments 100 to 120, wherein lyso-Gb1 is administered subcutaneously.

EMBODIMENT 122

The method of any one of embodiments 100 to 121, preferably embodiment 121, wherein lyso-Gb1 is administered over a period of time of at least two weeks, at least four weeks, at least six weeks, at least eight weeks, at least 10 weeks, or at least twelve weeks.

EMBODIMENT 123

The method of any one of embodiments 100 to 121, preferably any one of embodiments 121 to 122, wherein lyso-Gb1 is administered over a period of time of two weeks, four weeks, six weeks, eight weeks, 10 weeks or twelve weeks.

EMBODIMENT 124

The method of any one of embodiments 100 to 123, preferably any one of embodiments 121 to 123, the animal is a mouse.

EMBODIMENT 125

The method of embodiment 124, wherein the mouse is selected from the group comprising a C57BL/6JRj mouse, a C57BL/6 mouse and a C57/BL/10 mouse.

EMBODIMENT 126

The method of any one of embodiments 100 to 125, preferably any one of embodiments 121 to 125, wherein the at least one symptom is a peripheral symptom.

EMBODIMENT 127

The method of any one of embodiments 100 to 126, preferably embodiment 126, wherein the peripheral symptom is selected from the group comprising visceral enlargement of the spleen, mild anemia, inflammatory tissue response and visceral enlargement of the liver.

EMBODIMENT 128

The method of any one of embodiments 100 to 127, preferably any one of embodiments 121 to 127, wherein lyso-Gb1 is administered until the lyso-Gb1 concentration in the peripheral blood of the animal is about 500 ng/ml peripheral blood or more.

EMBODIMENT 129

The method of any one of embodiments 100 to 128, preferably any one of embodiments 121 to 128, wherein the disease is Gaucher disease selected from the group comprising mild form of Gaucher disease, type 1 Gaucher disease and non-neuronopathic Gaucher disease.

EMBODIMENT 130

The method according to any one of embodiments 100 to 120, wherein lyso-Gb1 is administered intrathecally.

EMBODIMENT 131

The method of any one of embodiments 100 to 120 and 130, preferably embodiment 130, wherein lyso-Gb1 is administered over a period of time of at least two weeks, at least four weeks, at least six weeks, at least eight weeks, at least 10 weeks, or at least twelve weeks.

EMBODIMENT 132

The method of any one of embodiments 100 to 120 and 130 to 131, preferably any one of embodiments 130 to 131, wherein lyso-Gb1 is administered over a period of time of two weeks, four weeks, six weeks, eight weeks, 10 weeks or twelve weeks.

EMBODIMENT 133

The method of any one of embodiments 100 to 120 and 130 to 132, preferably any one of embodiments 130 to 1323, the animal is a mouse.

EMBODIMENT 134

The method of embodiment 133, wherein the mouse is a C57BL/6JRj mouse, a C57BL/6 mouse and a C57/BL/10 mouse

EMBODIMENT 135

The method of any one of embodiments 100 to 120 and 130 to 134, preferably any one of embodiments 130 to 134, wherein the at least one symptom is a central nervous symptom.

EMBODIMENT 136

The method of any one of embodiments 100 to 120 and 130 to 135, preferably embodiment 135, wherein the central symptom is selected from the group comprising ataxia, dementia, ocular apraxia, and parkinsonism.

EMBODIMENT 137

The method of any one of embodiments 100 to 120 and 130 to 136, preferably any one of embodiments 130 to 136, wherein lyso-Gb1 is administered until the lyso-Gb1 concentration in the peripheral blood of the animal is about 10 to 30 ng/ml cerebrospinal fluid.

EMBODIMENT 138

The method of any one of embodiments 100 to 120 and 130 to 137, preferably any one of embodiments 130 to 137, wherein the disease is Gaucher disease selected from the group comprising type 2 Gaucher disease, type 3 Gaucher disease and neuronopathic Gaucher disease.

EMBODIMENT 139

An animal model obtainable by a method according to any one of embodiments 100 to 138, wherein the animal model is an animal model for a disease, preferably the disease is a lysosomal storage disease.

EMBODIMENT 140

An animal model, wherein the animal model is a lyso-Gb1 induced animal model for a disease, preferably the disease is a lysosomal storage disease.

EMBODIMENT 141

The animal model according to any one of embodiments 139 to 140, wherein the lysosomal storage disorder is a lysosomal storage disorder caused by a defective activity of glucocerebrosidase.

EMBODIMENT 142

The animal model according to any one of embodiments 139 to 141, wherein the disease is Gaucher disease, preferably the disease is at least one peripheral symptom of Gaucher disease, wherein preferably the at least one peripheral symptom of Gaucher disease is selected from the group comprising visceral enlargement of the spleen, mild anemia and inflammatory tissue response, more preferably at least one peripheral symptom of type 1, of type 2 and/or of type 3 Gaucher disease, most preferably of type 1 Gaucher disease.

EMBODIMENT 143

The animal model according to embodiment 142, wherein Gaucher disease is a mild form of Gaucher disease.

EMBODIMENT 144

The animal model according to embodiment 142, wherein Gaucher disease is non-neuronopathic Gaucher disease.

EMBODIMENT 145

The animal model according to embodiment 142, wherein Gaucher disease is a neuronopathic Gaucher disease.

EMBODIMENT 146

The animal model according to any one of embodiments 139 to 142, wherein the disease is selected from the group comprising type 1 Gaucher disease, type 2 Gaucher disease and type 3 Gaucher disease.

EMBODIMENT 147

The animal model according to embodiment 146, wherein the disease is type 1 Gaucher disease.

EMBODIMENT 148

The animal model according to any one of embodiments 139 to 146, wherein the disease is type 2 Gaucher disease or type 3 Gaucher disease.

EMBODIMENT 149

The animal model according to any one of embodiments 139 and 140, wherein the disease is Parkinson's disease.

EMBODIMENT 150

The animal model according to any one of embodiments 139 to 149, wherein the animal model is a lyso-Gb1 induced animal model.

EMBODIMENT 151

The animal model according to any one of embodiments 139 to 150, wherein the animal model is a mammal.

EMBODIMENT 152

The animal model according to embodiment 151, wherein the mammal is a rodent.

EMBODIMENT 153

The animal model according to embodiment 151, wherein the rodent is selected from the group comprising mouse and rat.

EMBODIMENT 154

The animal model according to embodiment 151, wherein the mammal is selected from the group comprising a primate, a dog, a pig and a sheep.

EMBODIMENT 155

The animal model according to embodiment 151, wherein the animal model is a mouse animal model.

EMBODIMENT 156

The animal model according to embodiment 155, wherein the mouse animal model is a lyso-Gb1 induced mouse animal model.

EMBODIMENT 157

The animal model according to embodiment 156, wherein the lyso-Gb1 induced mouse animal model is a lyso-Gb1 induced mouse animal model for Gaucher disease.

EMBODIMENT 158

The animal model according to embodiment 157, wherein Gaucher disease is selected from the group comprising mild form of Gaucher disease, type 1 Gaucher disease and non-neuronopathic Gaucher disease.

EMBODIMENT 159

A method for the screening of an agent suitable for and/or capable of treating and/or preventing a disease, wherein the method comprises
  testing whether a candidate compound is an antagonist of lyso-Gb1,
wherein if the candidate compound is an antagonist of lyso-Gb1, the candidate compound is an agent suitable for and/or capable of treating and/or preventing a disease.

EMBODIMENT 160

The method according to embodiment 159, wherein the antagonist of lyso-Gb1 is an antagonist as defined in any one of embodiments 72 to 85.

EMBODIMENT 161

The method according to any one of embodiments 159 to 160, wherein the candidate compound is selected from a small molecule, a lyso-Gb1 binding protein, a lyso-Gb1 binding peptide, an antibody or antigen-binding fragment thereof, an anticalin, an aptamer, a spiegelmer, a and a lyso-Gb1 degrading enzyme.

EMBODIMENT 162

The method according to any one of embodiments 159 to 161, wherein the testing whether a candidate compound is an antagonist for lyso-Gb1 is made in an animal model according to any one of embodiments 139 to 158 or is made using an animal model according to any one of embodiments 139 to 158.

EMBODIMENT 163

The method according to embodiment 162, wherein the method comprises administering the candidate to the animal model and determining whether the candidate compound ameliorates at least one symptom of the disease, preferably the at least one symptom is at least one peripheral symptom of Gaucher disease, wherein even more preferably the at least one peripheral symptom of Gaucher disease is selected from the group comprising visceral enlargement of the spleen, mild anemia and inflammatory tissue response, most preferably at least one peripheral symptom of type 1, of type 2 and/or of type 3 Gaucher disease, utmost preferably of type 1 Gaucher disease.

EMBODIMENT 164

The method according to any one of embodiments 159 to 163, wherein the candidate compound is contained in a library of compounds or is taken from a library of compounds.

EMBODIMENT 165

A method for the assessment of the effects of an agent in the treatment and/or prevention of a disease, wherein the method comprises testing the effect of the agent in an animal model according to any one of embodiments 139 to 158 or using an animal model according to any one of embodiments 139 to 158.

EMBODIMENT 166

The method according to embodiment 165, wherein the agent is an antagonist as defined in any one of embodiments 72 to 85.

EMBODIMENT 167

The method according to any one of embodiments 165 to 166, wherein the agent is selected from a small molecule, a lyso-Gb1 binding protein, a lyso-Gb1 binding peptide, an antibody or antigen-binding fragment thereof, an anticalin, an aptamer, a spiegelmer, and a lyso-Gb1 degrading enzyme.

EMBODIMENT 168

The method according to any one of embodiments 165 to 167, wherein the method comprises administering the agent to the animal model and determining whether the agent ameliorates at least one symptom of the disease, preferably the at least one symptom is at least one peripheral symptom of Gaucher disease, wherein even more preferably the at least one peripheral symptom of Gaucher disease is selected from the group comprising visceral enlargement of the spleen, mild anemia and inflammatory tissue response, most preferably at least one peripheral symptom of type 1, of type 2 and/or of type 3 Gaucher disease, utmost preferably of type 1 Gaucher disease.

EMBODIMENT 169

The method according to any one of embodiments 159 to 168, wherein the disease is a lysosomal storage disorder (LSD).

EMBODIMENT 170

The method according to any one of embodiments 159 to 169, wherein the lysosomal storage disorder is a lysosomal storage disorder caused by a defective activity of glucocerebrosidase.

EMBODIMENT 171

The method according to any one of embodiments 159 to 170, wherein the disease is Gaucher disease.

EMBODIMENT 172

The method according to embodiment 171, wherein Gaucher disease is a mild form of Gaucher disease.

EMBODIMENT 173

The method according to embodiment 171, wherein Gaucher disease is non-neuronopathic Gaucher disease.

EMBODIMENT 174

The method according to embodiment 171, wherein Gaucher disease is a neuronopathic Gaucher disease.

EMBODIMENT 175

The method according to any one of embodiments 159 to 171, wherein the disease is selected from the group comprising type 1 Gaucher disease, type 2 Gaucher disease and type 3 Gaucher disease.

EMBODIMENT 176

The method according to embodiment 175, wherein the disease is type 1 Gaucher disease.

EMBODIMENT 177

The method according to any one of embodiments 159 to 171, wherein the disease is type 2 Gaucher disease or type 3 Gaucher disease.

EMBODIMENT 178

The method according to any one of embodiment 139 to 168, wherein the disease is Parkinson's disease.

The present invention is based on the surprising finding that lyso-Gb1 is a target, and more specifically a druggable target, for a lysosomal storage disorder, preferably for Gaucher disease, and Parkinson disease. Another surprising finding underlying the present invention is that an animal model can be generated by using lyso-Gb1, more specifically by administering lyso-Gb1 to an animal over a period of time, whereupon said animal will develop at least one of the symptoms characteristic for the disease with the disease preferably being a lysosomal storage disorder, preferably Gaucher disease, or Parkinson's disease.

The present invention is further based on the surprising finding that lyso-Gb1 causes at least one peripheral symptom of Gaucher disease, whereby the at least one peripheral symptom of Gaucher disease is selected from the group comprising visceral enlargement of the spleen, mild anemia and inflammatory tissue response, more preferably at least one peripheral symptom of type 1, of type 2 and/or of type 3 Gaucher disease, utmost preferably of type 1 Gaucher disease. This finding is surprising as many other pathophysiological roles have been attributed to sphingolipids (Rotstein et al., 2010, J Lipid Res 51:1247-1262), lyso-sphingolipids (Ballabio et al., 2009, Biochem Biophys Act 1793:684-96), and in particular, lyso-Gb1 (Schueler et al., 2003 Neurobiol Dis 14: 595-601).

Lyso-Gb1 is also referred to herein as glucosylsphingosine or lyso-glucocerebroside and has the formula (I):

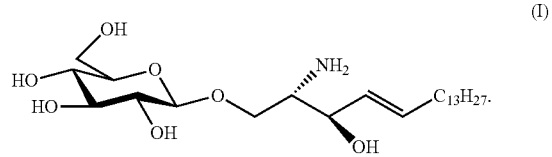

As preferable used herein in connection with each and any embodiment of each and any aspect of the present invention, the terms target and target molecule are used herein in an interchangeable manner.

As preferably used herein in connection with each and any embodiment of each and any aspect of the present invention a target molecule is a molecule which is targeted by another compound, preferably by an antagonist of the target, whereby preferably the compound interacts directly with the target molecule. In connection therewith, a direct interaction is preferably a physical interaction between the compound and the target molecule preferably including an interaction between atoms, ions and/or chemical groups or moieties of the target molecule with atoms, ions and/or chemical groups or moieties of the compound.

As preferably used herein in connection with each and any embodiment of each and any aspect of the present invention, a druggable target is a target molecule which when directly interacting with a compound in a subject suffering from a disease or being at risk of developing such disease results in treatment of the disease and/or prevention of the disease; preferably such compound is an antagonist of the target molecule and/or such direct interaction is preferably a physical interaction between the compound and the target molecule preferably including an interaction between atoms, ions and/or chemical groups or moieties of the target molecule with atoms, ions and/or chemical groups or moieties of the compound.

As preferably used herein in connection with each and any embodiment of each and any aspect of the present invention a candidate compound library is a library of candidate compounds. Preferably, the library comprises at least two or more elements, i.e. at least two or more compounds. Preferably, a candidate compound is a compound which interacts directly with a target molecule. In connection therewith, a direct interaction is preferably a physical interaction between the candidate compound and the target molecule preferably including an interaction between atoms, ions and/or chemical groups or moieties of the target molecule with atoms, ions and/or chemical groups or moieties of the candidate compound.

As preferably used herein in connection with each and any embodiment of each and any aspect of the present invention, a lysosomal storage disease (LSD) is a rare inherited metabolic disorder that results from defects in lysosomal function. LSDs result when a specific organelle in the body's cells—the lysosome—malfunctions.

As preferably used herein in connection with each and any embodiment of each and any aspect of the present invention, glucocerebrosidase is a glucocerebrosidase the activity of which is decreased compared to a healthy subject because of hereditary deficiency of said enzyme. Said deficiency results from recessive mutation(s) in the gene coding for glucocerebrosidase, a specific lysosomal hydrolase (also known as beta-glucosidase, EC 3.2.1.45, PDB 1OGS) located on chromosome 1 (1q21) and affects both males and females. Different mutations in the beta-glucosidase determine the remaining activity of the enzyme, and, to a large extent, the phenotype. Glucocerebrosidase is also referred to herein as β-glucocerebrosidase, beta-glucosidase, acid beta-glucosidase, glucosylceramidase or D-glucosyl-N-acyl-sphingosine glucohydrolase. The enzyme is a 55.6 KD, 497 amino acids long protein having glucosylceramidase activity, i.e. the enzyme catalyses the breakdown of a fatty substance called glucocerebroside by cleavage, i.e. hydrolysis, of a beta-glucosidic linkage of glucocerebroside, which is an intermediate in glycolipid metabolism. Glucocerebroside, also referred to herein as glucosylceramide or Gb1, is a cell membrane constituent of red and white blood cells. When the enzyme is defective, the substance accumulates, particularly in cells of the mononuclear cell lineage. This is because macrophages that clear these cells are unable to eliminate the waste product, which accumulates in fibrils, and turn into so called Gaucher cells, which appear on light microscopy to resemble crumpled-up paper. Fatty material can accumulate in the spleen, liver, kidneys, lungs, brain and bone marrow.

As preferably used herein in connection with each and any embodiment of each and any aspect of the present invention, Gaucher disease encompasses three subtypes on the basis of the age of onset and of signs of nervous system involvement. Type 1, the non-neuronopathic form, is the most common (>90% of patients), and major symptoms include enlargement of the spleen and liver (hepatosplenomegaly), thrombocytopenia, anaemia and skeletal disease (Mistry and Zimran, Dis. Model. Mech. 2011, November; 4(6): 746-752). Moreover, pronounced visceral inflammation in other organs such as the lungs has been reported, which is associated with the Infiltration of large, characteristic macrophages into the tissues ("Gaucher cells") and concomitance of inflammatory cytokines like of TNF-α, IL-1b, IL-6, and ChT1. In the neuronopathic forms, i.e. types 2 and 3 which are both also referred to as neuronal GD (nGD), whereby GD stands for Gaucher disease, and which are much more rare than type 1, neurological abnormalities are observed in addition to visceral symptoms.

In accordance therewith, and as preferably used herein in connection with each and any embodiment of each and any aspect of the present invention, Gaucher disease encompass Non-neuronopathic type I, also referred to herein as type 1, is the most common form of the disease, occurring in approximately 1 in 50,000 live births. It occurs most often among persons of Ashkenazi Jewish heritage. Symptoms may begin early in life or in adulthood and include enlarged liver and grossly enlarged spleen (together hepatosplenomegaly); the spleen can rupture and cause additional complications. Skeletal weakness and bone disease may be extensive. Spleen enlargement and bone marrow replacement cause anemia, thrombocytopenia and leukopenia. The brain is not affected pathologically, but there may be lung and, rarely, kidney impairment. Diseased subjects in this group usually bruise easily (due to low levels of platelets) and experience fatigue due to low numbers of red blood cells. Depending on disease onset and severity, type I patients may live well into adulthood. Many diseased subjects have a mild form of the disease or may not show any symptoms. Chronic neuronopathic type 2, also referred to herein as type 2, can begin at any time in childhood or even in adulthood, and occurs in approximately 1 in 100,000 live births. It is characterized by slowly progressive but milder neurologic symptoms compared to the acute or type 3 version. Major symptoms include an enlarged spleen and/or liver, seizures, poor coordination, skeletal irregularities, eye movement disorders, blood disorders including anemia and respiratory problems. Patients often live into their early teen years and adulthood.

Acute neuronopathic type 3, also referred to herein as type 3, typically begins within 6 months of birth and has an incidence rate of approximately 1 in 100,000 live births. Symptoms include an enlarged liver and spleen, extensive and progressive brain damage, eye movement disorders, spasticity, seizures, limb rigidity, and a poor ability to suck and swallow. Affected children usually die by age 2.

Preferably, symptoms of Gaucher disease may include enlarged spleen and liver, liver malfunction, skeletal disorders and bone lesions that may be painful, severe neurologic complications, swelling of lymph nodes and (occasionally) adjacent joints, distended abdomen, a brownish tint to the skin, anemia, low blood platelets and yellow fatty deposits on the white of the eye (sclera). Persons affected most seriously may also be more susceptible to infection.

As preferably used herein in connection with each and any embodiment of each and any aspect of the present invention, a subject is a human.

As preferably used herein in connection with each and any embodiment of each and any aspect of the present invention, a mouse animal model and a mouse model are used herein in an interchangeable manner.

If, in connection with each and any aspect of the present invention and if not explicitly indicated otherwise, reference is made to a disease or disorder, such disease and disorder, respectively, is either a lysosomal storage disorder or Parkinson's disease. It is within the present invention that the lysosomal storage disorder is typically a lysosomal storage disorder caused by a defective activity of glucocerebrosidase. Preferably, defective activity of glucocerebrosidase means that the enzymatic activity of the glucocerebrosidase is reduced compared to the activity of an enzymatic activity of glucocerebrosidase of a healthy individual, whereby preferably such individual is a human being. More preferably such defective activity of glucocerebrosidase is caused by one or several mutations, preferably amino acid mutations. Insofar, defective activity of glucocerebrosidase means and/or encompasses embodiments where the enzyme is defective compared to the enzyme of a healthy individual, whereby preferably such individual is a human being.

In an embodiment of each and any aspect of the present invention the lysosomal storage disorder is Gaucher disease. It will be acknowledged by a person skilled in the art that Gaucher disease exists in various forms, whereby it is understood in the art that the various forms actually constitute a continuum. Nevertheless, even to date Gaucher disease is differentiated as or categorized as type 1 Gaucher disease, type 2 Gaucher disease and type 3 Gaucher disease. Type 1 Gaucher is preferably also referred to as mild form of Gaucher disease or non-neuronopathic Gaucher disease. In contrast thereto, type 2 Gaucher disease and type 3 Gaucher disease are also referred to as neuronopathic Gaucher disease. It is also within the present invention that Gaucher disease is a severe form of Gaucher disease.

If, in connection with each and any aspect of the present invention and if not explicitly indicated otherwise, reference is made to an animal model, such animal model is preferably an animal model for a disease, preferably for any disease as disclosed herein and more preferably a lysosomal storage disease as defined herein including its various embodiments or Parkinson's disease.

In an embodiment of each and any aspect of the present invention, the animal model is a mammal. In a preferred embodiment the mammal is a rodent, wherein more preferably the rodent is selected from the group comprising a mouse, a rat, a rabbit and a Guinea pig. In another embodiment the animal is a dog, a sheep, a pig and a primate; preferably the primate is different from a human being. It will be acknowledged by a person skilled in the art that in accordance with the present invention an animal model can be generated based on any animal and any mammal in particular for which lyso-Gb1 is toxic and/or which is susceptible to lysosomal storage diseases and/or which shows glucocerebrosidase activity.

In connection with the present invention the subject undergoing any method of treatment and/or any method of prevention in accordance with the instant invention is preferably a human being. Also, when reference is made to an organism and without the organism being specified further, such organism is preferably a human being; alternative, such organism is different from a human being.

It will be understood that in a preferred embodiment of any aspect of the present invention treatment and/or prevention of Gaucher disease is treatment and/or prevention of at least one peripheral symptom of Gaucher disease, wherein preferably the at least one peripheral symptom of Gaucher disease is selected from the group comprising visceral enlargement of the spleen, mild anemia and inflammatory tissue response, more preferably at least one peripheral symptom of type 1, of type 2 and/or of type 3 Gaucher disease, most preferably of type 1 Gaucher disease.

It will be understood that in a preferred embodiment of any aspect of the present invention that a subject to be treated or treatable in accordance with the present invention is a subject who has been diagnosed as suffering from Gaucher disease. Methods for the diagnosis are known to the person skilled in the art and, for example, described in international patent application WO 2012/167925 and in Rolfs A et al. (Rolfs A et al., PLOS ONE, November 2013, vol. 8, issue 11, e79732), the disclosure of which is incorporated herein by reference. More specifically, a subject is diagnosed as suffering from Gaucher disease is the concentration of free lyso-Gb1 beyond a cut-off value, wherein the cut-off value is 5 ng/ml or 12 ng/ml in case the sample is a serum or plasma sample from the subject, whereby such serum or plasma sample may be one of a dry blood filter card, and wherein the cut-off value is 20 ng/ml in case the sample is blood and more preferably whole blood from the subject, whereby such blood or whole blood sample may be one of a dry blood filter card. As preferably used herein, free lyso-Gb1 refers to lyso-Gb1 which is as such present in a sample from the subject, such as blood, and, preferably, not the result of a manipulation of the sample of said subject. Such manipulation of a sample can be the one described by Groener et al. (Groener et al. Plasma glucosylceramide and ceramide in type 1 Gaucher disease patients: Correlations with disease severity and response to therapeutic intervention. Biochimica et Biophysica Acta 1781(2908)72~78, 2007). In accordance therewith, free lyso-Gb1 which is present as such in the blood of a subject from whom the sample is taken, is more particularly not a lyso-Gb1 which is generated by chemical, biochemical or physical treatment of the sample contained in the blood and sample, respectively, preferably outside of the body of the patient. It will be also understood by a person skilled in the art that free lyso-Gb1 as used herein, preferably is present in addition to Gb1 and is a compound produced by the subject's metabolic activities. Accordingly, Gb1, which is the molecule that is accumulated in connection with Gaucher's disease is present in the sample from the subject has compared to the molecule in a free lyso form, i.e. free-lyso-Gb1, present in the blood of the subject at least one fatty acid moiety linked to the primary amino group of the sphingosine moiety of lyso-Gb1.

If, in connection with each and any aspect of the present invention and if not explicitly indicated otherwise, reference is made to an antagonist of lyso Gb1, such antagonist is, in one embodiment, capable of reducing or ameliorating at least one symptom of a disease. I a further embodiment, the capable of or suitable for treating a disease. In an embodiment, the antagonist is capable of reducing or ameliorating at least one symptom of a disease in an animal model of the disease, preferably the animal model is an animal model of the present invention. In an embodiment, the antagonist is capable of or suitable for treating a disease in an animal model of the disease, preferably the animal model is an animal model of the present invention in its various embodiments. In an embodiment of the antagonist of lyso-Gb1 the disease is any disease as disclosed herein and more preferably a lysosomal storage disease as defined herein including its various embodiments or Parkinson's disease.

In an embodiment, the antagonist is a compound selected from the group comprising a small molecule, a lyso-Gb1 binding protein, a lyso-Gb1 binding peptide, an antibody or antigen-binding fragment thereof, an aptamer, a spiegelmer and a lyso-Gb1 degrading enzyme.

In an embodiment, a small molecule is a chemical compound complying with the Lepinski's rules of five known to the ones skilled in the art. More specifically, according to said Lepinski's rules of a chemical compound qualifying as a small molecule has no more than one violation of the following criteria: (a) No more than 5 hydrogen bond donors (the total number of nitrogen-hydrogen and oxygen-hydrogen bonds); (b) no more than 10 hydrogen bond acceptors (all nitrogen or oxygen atoms), (c) a molecular mass less than 500 Daltons; and (d) an octanol-water partition coefficient log P not greater than 5.

In an embodiment, a lyso-Gb1 binding protein is a protein which binds lyso-Gb1 to an extent such that at least one of the above criteria in terms of reducing or ameliorating at least one symptom of a/the disease and, respective, treating a/the disease, each in the diverse embodiments disclosed herein, is fulfilled. In an embodiment the protein is a polymer comprising a chain of amino acid covalently linked through a peptide bond, whereby the polymer comprises about 100 amino acid residues or more. An embodiment of a lyso-Gb1 binding protein is a lyso-Gb1 binding antibody or lyso-Gb1 binding fragment thereof. A further lyso-Gb1 binding protein is a lyso-Gb1 binding anticalin.

Methods for the generation of an antibody binding to a distinct target, are known in the art. and, for example, described in Harlow, E., and Lane, D., "Antibodies: A Laboratory Manual," Cold Spring Harbor Laboratory, Cold Spring Harbor, N.Y., (1988). An antibody may be a monoclonal antibody or a polyclonal antibody. Preferably, monoclonal antibodies may be manufactured according to the protocol of Cesar and Milstein and further developments based thereon. Antibodies as used herein, include, but are not limited to, complete antibodies, antibody fragments or derivatives such as Fab fragments, Fc fragments and single-stranded antibodies, as long as they are suitable and capable of binding to lyso-Gb1. The generation of polyclonal antibodies is also known to the one skilled in the art and, for example, described in Harlow, E., and Lane, D., "Antibodies: A Laboratory Manual," Cold Spring Harbor Laboratory, Cold Spring Harbor, N.Y., (1988). Preferably, the antibodies used for therapeutic purposes are humanized or human antibodies as defined above.

The antibodies of the present invention and which may be used according to the present invention may have one or several markers or labels. Such markers or labels may be useful to detect the antibody either in its diagnostic application or its therapeutic application. Preferably the markers and labels are selected from the group comprising avidine, streptavidine, biotin, gold and fluorescein and used, e. g., in ELISA methods. These and further markers as well as methods are, e. g. described in Harlow, E., and Lane, D., "Antibodies: A Laboratory Manual," Cold Spring Harbor Laboratory, Cold Spring Harbor, N.Y., (1988).

It is also within the present invention that the label or marker exhibits an additional function apart from detection, such as interaction with other molecules. Such interaction may be, e.g., specific interaction with one or several other compounds. These other compounds may either be those inherent to the system where the antibody is used such as the human or animal body or the sample which is analysed by using the respective antibody. Appropriate markers may, for example, be biotin or fluoresceine with the specific interaction partners thereof such as avidine and streptavidine and the like being present on the respective compound or structure to interact with the thus marked or labelled antibody.

In an embodiment, a lyso-Gb1 binding peptide is a protein which binds lyso-Gb1 to an extent such that at least one of the above criteria in terms of reducing or ameliorating at least one symptom of a/the disease and, respective, treating a/the disease, each in the diverse embodiments disclosed herein, is fulfilled. In an embodiment the peptide is a polymer comprising a chain of amino acid covalently linked through a peptide bond, whereby the polymer comprises less than 100 amino acid residues. As used herein, the term peptide comprises also polypeptides typically comprising from about 10 to about 100 amino acid residues, and peptide in the narrower sense typically comprising 2 to about 10 amino acid residues. In an embodiment, lyso-Gb1 binding peptide is a lyso-Gb1 binding anticalin.

Anticalins a target binding polypeptides which are, among others, described in German patent application DE 197 42 706.

Aptamers are D-nucleic acids which are either single stranded or double stranded and which specifically interact with a target molecule. The manufacture or selection of aptamers is, e. g., described in European patent EP 0 533 838. Basically, the following steps are realized. First, a mixture of nucleic acids, i. e. potential aptamers, is provided whereby each nucleic acid typically comprises a segment of several, preferably at least eight subsequent randomised nucleotides. This mixture is subsequently contacted with the target molecule whereby the nucleic acid(s) bind to the target molecule, such as based on an increased affinity towards the target or with a bigger force thereto, compared to the candidate mixture. The binding nucleic acid(s) are/is subsequently separated from the remainder of the mixture. Optionally, the thus obtained nucleic acid(s) is amplified using, e. g. polymerase chain reaction. These steps may be repeated several times giving at the end a mixture having an increased ratio of nucleic acids specifically binding to the target from which the final binding nucleic acid is then optionally selected. These specifically binding nucleic acid(s) are referred to aptamers. It is obvious that at any stage of the method for the generation or identification of the aptamers samples of the mixture of individual nucleic acids may be taken to determine the sequence thereof using standard techniques. It is within the present invention that the aptamers may be stabilized such as, e. g., by introducing defined chemical groups which are known to the one skilled in the art of generating aptamers. Such modification may for example reside in the introduction of an amino group at the 2'-position of the sugar moiety of the nucleotides. Aptamers are currently used as therapeutical agents. However, it is also within the present invention that the thus selected or generated aptamers may be used for target validation and/or as lead substance for the development of medicaments, preferably of medicaments based on small molecules. This is actually done by a competition assay whereby the specific interaction between the target molecule and the aptamer is inhibited by a candidate drug whereby upon replacement of the aptamer from the complex of target and aptamer it may be assumed that the respective drug candidate allows a specific inhibition of the interaction between target and aptamer, and if the interaction is specific, said candidate drug will, at least in principle, be suitable to block the target and thus decrease its biological availability or activity in a respective system comprising such target. The thus obtained small molecule may then be subject to further derivatisation and modification to optimise its physical, chemical, biological and/or medical characteristics such as toxicity, specificity, biodegradability and bioavailability. In a preferred embodiment, the aptamer is an aptamer capable of binding to lyso-Gb1.

The generation or manufacture of spiegelmers which may be used or generated according to the present invention is based on a similar principle. The manufacture of spiegelmers is described in the international patent application WO 98/08856. Spiegelmers are L-nucleic acids, which means that they are composed of L-nucleotides rather than aptamers which are composed of D-nucleotides as aptamers are. Spiegelmers are characterized by the fact that they have a very high stability in biological system and, comparable to aptamers, specifically interact with the target molecule against which they are directed. In the purpose of generating spiegelmers, a heterogonous population of D-nucleic acids is created and this population is contacted with the optical antipode of the target molecule which is lyso-Gb1. Subsequently, those D-nucleic acids are separated which do not interact with the optical antipode of the target molecule. However, those D-nucleic acids interacting with the optical antipode of the target molecule are separated, optionally determined and/or sequenced and subsequently the corresponding L-nucleic acids are synthesized based on the nucleic acid sequence information obtained from the D-nucleic acids. These L-nucleic acids which are identical in terms of sequence with the aforementioned D-nucleic acids interacting with the optical antipode of the target molecule, will specifically interact with the naturally occurring target molecule rather than with the optical antipode thereof. Similar to the method for the generation of aptamers it is also possible to repeat the various steps several times and thus to enrich those nucleic acids specifically interacting with the optical antipode of the target molecule.

In connection with the various aspects of the present invention it is indicated that the disease is a lysosomal storage disease, preferably Gaucher disease. The instant application provides experimental evidence in terms of lyso-Gb1 being a target, preferably a druggable target, and capable of inducing and generating, respectively, an animal model for such disease. Based on said experimental evidence and the titre of lyso-Gb1 observed in patients suffering from Parkinson's disease, it is acknowledged and appreciated by a person skilled in the art that the same functions annotated to and exercised by lyso-Gb1 in connection with lysosomal storage disorder and Gaucher disease in particular, will be equally shown and exercised by lyso-Gb1 in Parkinson's disease. In an embodiment, Parkinson's disease is Parkinson's disease of a subject having a mutant glucocerebrosidase, preferably a mutant glucocerebrosidase as observed in subjects suffering from Gaucher disease, whereby more preferably the subject suffering from Parkinson's disease does not show any clinical sign of Gaucher disease.

The lyso-Gb1 degrading enzyme is in an embodiment a lyso-Gb1 metabolizing enzyme. Such kind of enzyme is suitable for use as an antagonist of lyso-Gb1 under the proviso that the lyso-Gb1 derivative obtained upon the enzyme having acted on lyso-Gb1 is no longer an antagonist of lyso-Gb1 is defined in connection with the present invention.

In a first aspect, the problem underlying the present invention is solved by the use of lyso-Gb1 as a target in the treatment of a disease. Such use is also referred to herein as the use according to the invention, the therapeutic use of lyso-Gb1 according to the invention, or the first use according to the present invention. Such first aspect is based on the surprising finding that lyso-Gb1 which has been identified recently as a diagnostic marker for Gaucher disease (Dekker N et al., Blood. 118(16):e118-27; Rolfs A et al., PLoS One. 8(11):e79732) is a target in a disease, preferably a lysosomal storage disease in its various embodiments disclosed herein, and Parkinson's disease. More importantly, lyso-Gb1 is also a druggable target. As preferably used herein, a druggable target is known to or is predicted to bind with high affinity to a drug.

Furthermore, by definition, the binding of the drug to a druggable target must alter the function of the target with a therapeutic benefit to the patient.

The use according to the first aspect of the present invention encompasses both in vitro and in vivo use. In the embodiment where the use is an in vitro use, lyso-Gb1 is used in a chemical, biochemical, physical or cell-based assay. Such assay determines, for example, whether a drug candidate is effective in binding to lyso-Gb1 and/or interfering with its action resulting in one or several of the symptoms of the disease. In an embodiment, the target is present outside of a cell, tissue, organ or organism; in an alternative embodiment, the target is present within a cell, tissue, organ or organism; such cell, tissue, organ or organism can be either alive or dead. In a further embodiment, the use is an in vivo use, i.e. the lyso-Gb1 as target is targeted for the purpose of treating and/or preventing a disease; preferably, in such embodiment lyso-Gb1 being present in an organism, organ, tissue or cell, which are more preferably alive. In an alternative embodiment, the in vivo use of lyso-Gb1 as target is not for the purpose of treatment and/or prevention of a disease; preferably, such in vivo use is for obtaining medical and/or scientific insights as to the involvement of lyso-Gb1 in a cell, tissue, organ or an organism.

In a second aspect, the problem underlying the present invention is solved by the use of lyso-Gb1 as a target in the development of a drug, whereby, preferably, the drug is capable of and/or suitable for treating and/or preventing a disease preferably a lysosomal storage disease in its various embodiments disclosed herein, and Parkinson's disease. Like the first aspect, this second aspect is based on the surprising finding that lyso-Gb1 is not only a diagnostic marker but a target in a disease, preferably a lysosomal storage disease in its various embodiments disclosed herein, and Parkinson's disease. Such second aspect is also referred to herein as the use according to the present invention, more specifically, the second use according to the present invention.

It will be understood that any embodiment of the first aspect of the present invention is also an embodiment of the second aspect of the present invention and vice versa.

As preferably used herein, the term "development of a drug" preferably means any process which provides a drug which is capable of and/or suitable for treating, preferably, a lysosomal storage disease in its various embodiments disclosed herein, and Parkinson's disease. Such process encompasses any screening for a drug, testing of any drug candidate as to their usefulness or fitness for a distinct purpose, including quality control, preferably quality control. Such development of a drug is different from preparation of a medicament, whereby preferably preparation of a medicament means formulating and/or packing of a drug so that it is ready for use by a patient or health care worker. In connection with such second aspect of the present invention, the drug, in an embodiment, is an antagonist according to the present invention.

In a third aspect, the problem underlying the present invention is solved by the use of lyso-Gb1 in the generation of an animal model of a disease, preferably a lysosomal storage disease in its various embodiments disclosed herein, and Parkinson's disease. This third aspect is based on the surprising finding that an animal model for this kind of disease can be generated by using lyso-Gb1. Such third aspect is also referred to herein as the use according to the present invention, more specifically, the third use according to the present invention.

The animal used in the generation is any animal disclosed herein. The animal model obtained by using lyso-Gb1 in accordance with the third aspect of the present invention is also referred to as lyso-Gb1 induced animal model. The disease for which the animal model is a model is a lysosomal storage disease as disclosed herein, or Parkinson's disease.

In a fourth aspect, the problem underlying the present invention is solved by an antagonist of lyso-Gb1 for use in the treatment and/or prevention of a disease, preferably a lysosomal storage disease in its various embodiments disclosed herein, and Parkinson's disease. This fourth aspect is based on the surprising finding that lyso-Gb1 is not only a diagnostic marker but a druggable target in a disease, preferably a lysosomal storage disease in its various embodiments disclosed herein, and Parkinson's disease. Such fourth aspect is also referred to herein as the antagonists according to the present invention.

As disclosed herein, the antagonist of the present invention can be prepared using routine measures and without any undue burden in light of the above surprising finding underling the present invention. In an embodiment, an antagonist of lyso-Gb1 is an antagonist preventing or ameliorating at least one disease related symptom shown by the animal model of the present invention.

In a fifth aspect, the problem underlying the present invention is solved by the use of an antagonist of lyso-Gb1 in the manufacture of a medicament, whereby the medicament is for treatment and/or prevention of a disease, preferably a lysosomal storage disease in its various embodiments disclosed herein, and Parkinson's disease. Like the fourth aspect of the present invention, this fifth aspect is based on the surprising finding that lyso-Gb1 is not only a diagnostic marker but a druggable target in a disease, preferably a lysosomal storage disease in its various embodiments disclosed herein, and Parkinson's disease. Such fifth aspect is also referred to herein as the use according to the present invention, more specifically, the fifth use according to the present invention.

In a sixth aspect, the problem underlying the present invention is solved by a method for the generation of an animal model for a disease, wherein the method comprises
a) administering to an animal lyso-Gb1 over a period of time,
b) determining whether the animal shows at least one symptom of the disease,
preferably a lysosomal storage disease in its various embodiments disclosed herein, and Parkinson's disease. This sixth aspect is based on the surprising finding that an animal model for this kind of disease can be generated by using lyso-Gb1, wherein the animal model is an animal model for a disease, preferably a lysosomal storage disease in its various embodiments disclosed herein, and Parkinson's disease. Such sixth aspect is also referred to herein as the method for the generation of an animal model according to the present invention. As the animal model is generated by the use of lyso-Gb1, the animal model obtained or obtainable from such method of the present invention is also referred to as lyso-Gb1 induced animal model.

In an embodiment, lyso-Gb1 is continuously administered over the period of time.

In an embodiment of the method for the generation of an animal model according to the present invention, the animal provided in step a) is typically a healthy animal which is treated so to develop the phenotype of the disease, at least one symptom of said disease.

A preferred animal is mouse. It will be acknowledged by a person skilled in the art that typically, a mouse of young age such as 10 weeks is used. It is, however, also within the present invention that an even younger or older mouse is used.

In an embodiment according to the present invention, lyso-Gb1 is administered to the animal until at least one symptom of the disease is displayed by the animal. Preferably, the at least one symptom of the disease is stably displayed. As preferably used herein, stably displayed means that the at least one symptom of the disease is displayed by the animal for a time sufficient so as to carry out the tests and procedures for which the animal model is used.

It will be acknowledged by a person skilled in the art that the concentration of lyso-Gb1 administered to the animal depends on the period of time over which lyso-Gb1 is administered and, respectively, to be administered, and the desired and intended, respectively, severity of the disease. In light of the instant disclosure, the concentration may be determined by routine experiments. Preferably, lyso-Gb1 is administered to an extent such that an intoxication, preferably a chronic intoxication is achieved. In case of non-neuronopathic Gaucher disease, systemic chronic intoxication is to be achieved, whereas in case of neuronopathic Gaucher disease chronic CNS intoxication is to be achieved.

It will be acknowledged by a person skilled in the art that for non-neuronopathic Gaucher disease subcutaneous administration is preferred, whereas for neuronopathic Gaucher disease intrathecal administration is preferred. In case of subcutaneous administration a possible daily dosage is 10 mg lyso-Gb1/kg body weight, whereby the lyso-Gb1 is continuously administered subcutaneously by means of pumps with a flow rate of 2.64 µl/day.

As to the specific animal strain and mouse strain used in the method of the present invention for the generation of an animal model it will be acknowledged by a person skilled in the art that, in principle, any wild type laboratory strain can be used. Such wild type laboratory strand is one selected from the group comprising C57BL/6JRj strain, a C57BL/6 strain, and C57/BL/10 strain.

In an embodiment, the at least one symptom of the disease, preferably in case of the disease being Gaucher disease and more preferably non-neuronopathic Gaucher disease, is a peripheral symptom. Preferably, such peripheral symptom is one selected from the group comprising visceral enlargement of the spleen, mild anemia, inflammatory tissue response and visceral enlargement of the liver. As to enlargement of the liver and spleen, it will be acknowledged by a person skilled in the art that such enlargement is relative to a non-lyso-Gb1 treated, animal which thus effectively acts as a negative control. As preferably used herein, anemia is defined as "Hb values 2× SD below the baseline value" (Raabe B M et al., J Am Assoc Lab Anim Sci. 50(5):680-5). Mild form of anemia is this one where the observed Hb values are not much below, i.e. close to the baseline value. As preferably used herein, inflammatory tissue response is determined based on CD68 and F4/80 as known in the art (see, e.g., Boven L A et al., Am J. Clin Pathol 2004 122(3): 359-69).

In an embodiment, the at least one symptom of the disease, preferably in case of the disease being Gaucher disease and more preferably neuronopathic Gaucher disease, is central nervous symptom. Preferably, such central nervous symptom is one selected from the group comprising ataxia, dementia, ocular apraxia, and parkinsonism.

In a seventh aspect, the problem underlying the present invention is solved by an animal model obtainable by a method according to the sixth aspect, wherein the animal model is an animal model for a disease, preferably a lysosomal storage disease in its various embodiments disclosed herein, and Parkinson's disease. Like the sixth aspect of the present invention, this seventh aspect is based on the surprising finding that an animal model for this kind of disease can be generated by using lyso-Gb1. Such seventh aspect is also referred to herein as the animal model according to the present invention.

In an eighth aspect, the problem underlying the present invention is solved by an animal model, wherein the animal model is a lyso-Gb1 induced animal model for a disease, preferably a lysosomal storage disease in its various embodiments disclosed herein, and Parkinson's disease. Like the seventh aspect of the present invention, this eighth aspect is based on the surprising finding that an animal model for this kind of disease can be generated by using lyso-Gb1. Such eighth aspect is also referred to herein as the animal model according to the present invention.

In a ninth aspect, the problem underlying the present invention is solved by a method for the screening of an agent suitable for and/or capable of treating and/or preventing a disease, wherein the method comprises
testing whether a candidate compound is an antagonist of lyso-Gb1,
wherein if the candidate compound is an antagonist of lyso-Gb1, the candidate compound is an agent suitable for and/or capable of treating and/or preventing a disease. Preferably, the disease is a lysosomal storage disease in its various embodiments disclosed herein, and Parkinson's disease. This ninth aspect is based on the surprising finding that that lyso-Gb1 is not only a diagnostic marker but a druggable target in a disease, preferably a lysosomal storage disease in its various embodiments disclosed herein, and Parkinson's disease. Such ninth aspect is also referred to herein as the method for the screening of an agent suitable for and/or capable of treating and/or preventing a disease according to the present invention.

In an embodiment of the method for the screening of an agent suitable for and/or capable of treating and/or preventing a disease according to the present invention, the testing comprises the use of an animal model of the present invention. Preferably, said testing comprises administering to the animal model the candidate compound and assessing whether the candidate compound reduces or ameliorates at least one symptom of the disease displayed by the animal model.

In an embodiment of the method for the screening of an agent suitable for and/or capable of treating and/or preventing a disease according to the present invention, the antagonist of lyso-Gb1 is an antagonist according to the present invention. In another embodiment, the candidate compound is a compound small molecule, a lyso-Gb1 binding protein, a lyso-Gb1 binding peptide, an antibody or antigen-binding fragment thereof, an anticalin, an aptamer, a spiegelmer, a and a lyso-Gb1 degrading enzyme.

In a tenth aspect, the problem underlying the present invention is solved by a method for the assessment of the effects of an agent in the treatment and/or prevention of a disease, wherein the method comprises testing the effect of the agent in an animal model according to the present invention or using an animal model according to the present invention.

Preferably, the disease is a lysosomal storage disease in its various embodiments disclosed herein, and Parkinson's disease. This tenth aspect is based on the surprising finding that lyso-Gb1 is not only a diagnostic marker but a druggable target in a disease, preferably a lysosomal storage disease in its various embodiments disclosed herein, and Parkinson's disease. Such tenth aspect is also referred to herein as the method for the assessment of the effects of an agent in the treatment and/or prevention of a disease according to the present invention.

The method for the assessment of the effects of an agent in the treatment and/or prevention of a disease according to the present invention is, in an embodiment, used for assessing one of the following effects of the agent: side effects, synergistic effects, toxic effect, effects on various physiological parameters, effects on biochemical factors and parameters. Such effects are known to the one skilled in the art and assays for determining such effects are equally known to a person skilled in the art. It will also be understood by a person skilled in the art that in such method at least a negative control and, optionally a positive control will be subjected to said method. Based on such negative control, any advantageous effect associated with a tested agent can be identified and, optionally, quantified. This method of the invention is, in an embodiment used in the profiling of an agent and drug candidate, respectively. Such profiling is part of the preparation of a dossier for submission to health authorities when applying for a market authorization for an agent to be used in the treatment and/or prevention of a disease.

The present invention is now further illustrated by the following figures and examples from which further features, embodiments and advantages may be taken.

More specifically:

FIGS. 1A and 1B are diagrams showing the level of lyso-Gb1 in blood of mice treated with either lyso-Gb1 or vehicle alone, as a function of time with FIG. 1A presenting the results as a bar diagram and FIG. 1B presenting the results as a boxplot; mice received subcutaneous lyso-Gb1 for 12 weeks using osmotic mini pumps; lyso-Gb1 values were increased at first sampling after 4 weeks, and throughout the treatment phase thereafter; vehicle-treated (or pre-dose) animals had lower, yet detectable lyso-Gb1 values of 1.2-1.5 ng/mL blood; the number of animals tested is indicated in the figure for each data point the boxes indicate the median and 25th and 75th percentiles, the whiskers of the graph show the minimum and maximum values.

FIG. 2A is a diagram showing lyso-Gb1 concentration (ng/ml dry tissue) in various tissues, namely heart, kidneys, liver, spleen and brain; lyso-Gb1 treated animals are shown as black, vehicle-treated animals as white boxes indicating the min and max values of three independent animals whereas each organ sample has been measured in duplicates; the white and black lines indicate the mean values; all peripheral organs of treated mice showed strongly elevated levels of lyso-Gb1 compared to control animals;

FIG. 2B is a diagram showing lyso-Gb1 concentration (ng/ml urine) in urine that was collected for 24 hr from one group of 4 (untreated) and two groups of 3 (treated) animals per cage at 6 weeks after treatment start. The obtained lyso-Gb1 levels are indicated above the respective column. Lyso-Gb1 content in the treated animals refer to a calculated excretion rate of 0.6 ng*min-1; lyso-Gb1 treated animals are shown as black, vehicle-treated animals as white boxes, indicating the minimum and maximum values of three animals, whereas each organ sample has been measured in duplicates. The white and black lines indicate the mean values.

FIG. 3 is a panel of two diagrams showing blood changes in lyso-Gb1 treated C57/BL/6JRj mice for Hb (hemoglobin; left diagram) and Hct (haematocrit; right diagram); values were derived from 4 control and 6 lyso-Gb1 treated mice at each indicated time point (4 weeks, 8 weeks and 12 weeks); the black and white boxes indicate the median, 25th and 75th percentile, the whiskers of the graph show the largest and smallest values; differences between treatment groups at each time point were analyzed using two-tailed Mann-Whitney test. Left panel: Hb values were 2× SD below the baseline value at each time point, indicating mild anemia. Right panel: Hct values significantly differed at 4 and 8 weeks after treatment initiation.

FIG. 4A is a panel of two diagrams showing the result of organ weight analysis for spleen and liver after 8 and 12 weeks (g/100 g body weight); values were derived from 4 control and 6 lyso-Gb1 treated mice at each indicated time point; the black and white boxes indicate the median, 25th and 75th percentile, the whiskers of the graph show the largest and smallest values; differences between treatment groups at each time point were analyzed using two-tailed Mann-Whitney test; the spleens of treated mice were enlarged versus controls 8 and 12 weeks after treatment initiation. Liver weight was not statistically significantly different compared with controls.

FIGS. 5A-B are microphotographs showing H&E-stained spleen sections from vehicle and lyso-Gb1 treated mice showed similar splenic architecture with white and red pulp (FIG. 5A, B).

Figure 5:
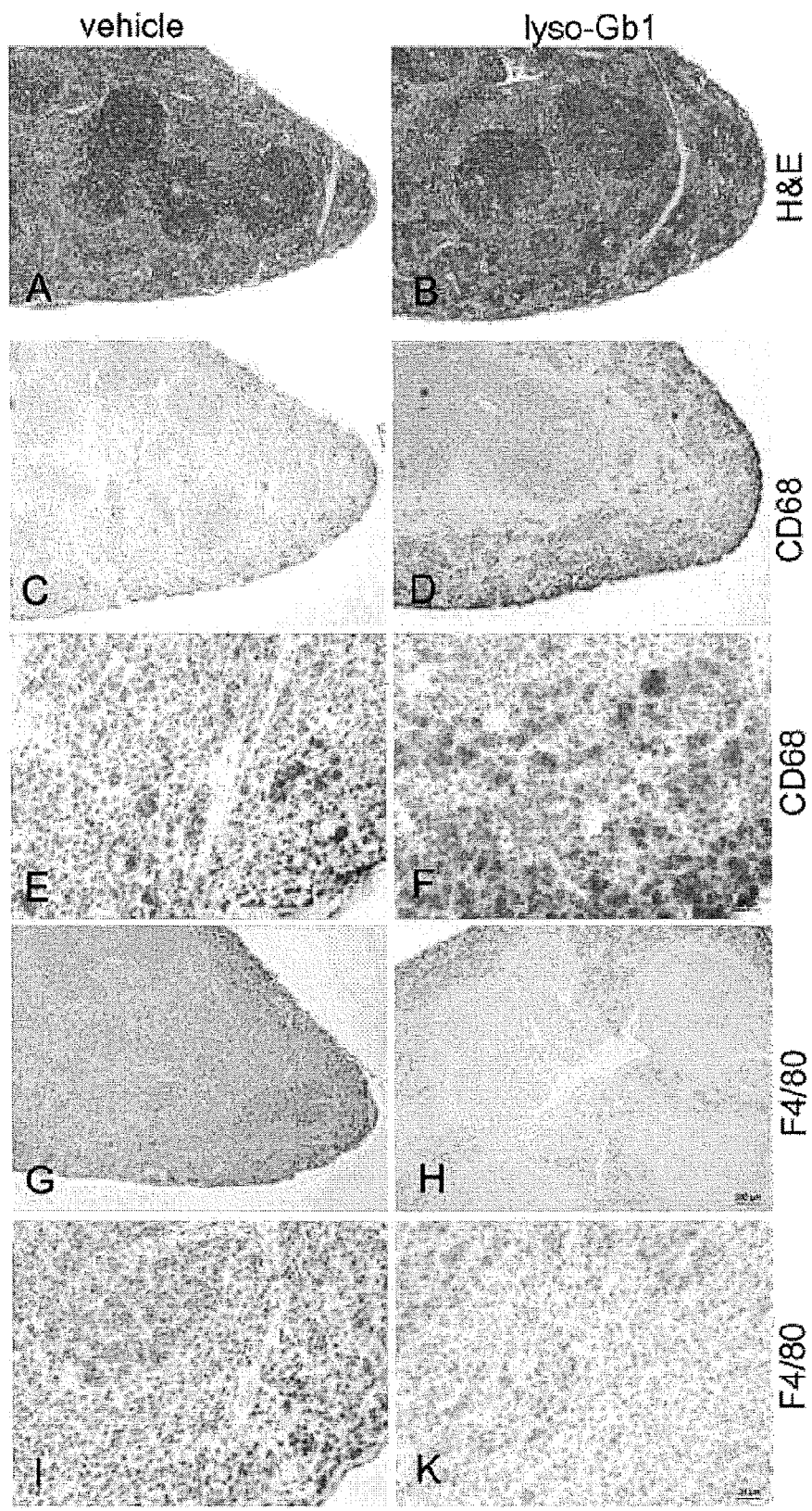

FIGS. 5 C-J are microphotographs showing paraffin sections from spleen of vehicle and lyso-Gb1 treated mice were immunohistochemically analyzed with anti-CD68 (FIG. 5C, D and high magnification E, F) and anti-F4/80 (FIG. 5G, H and high magnification I, J), whereas section from lyso-Gb1 treated mice showed a marked increase of the number of CD68 and F4/80 positive cells in comparison to vehicle controls.

FIG. 6 shows tables 1A and 1B that comprises all parameters tested in the study.

Figure 7:
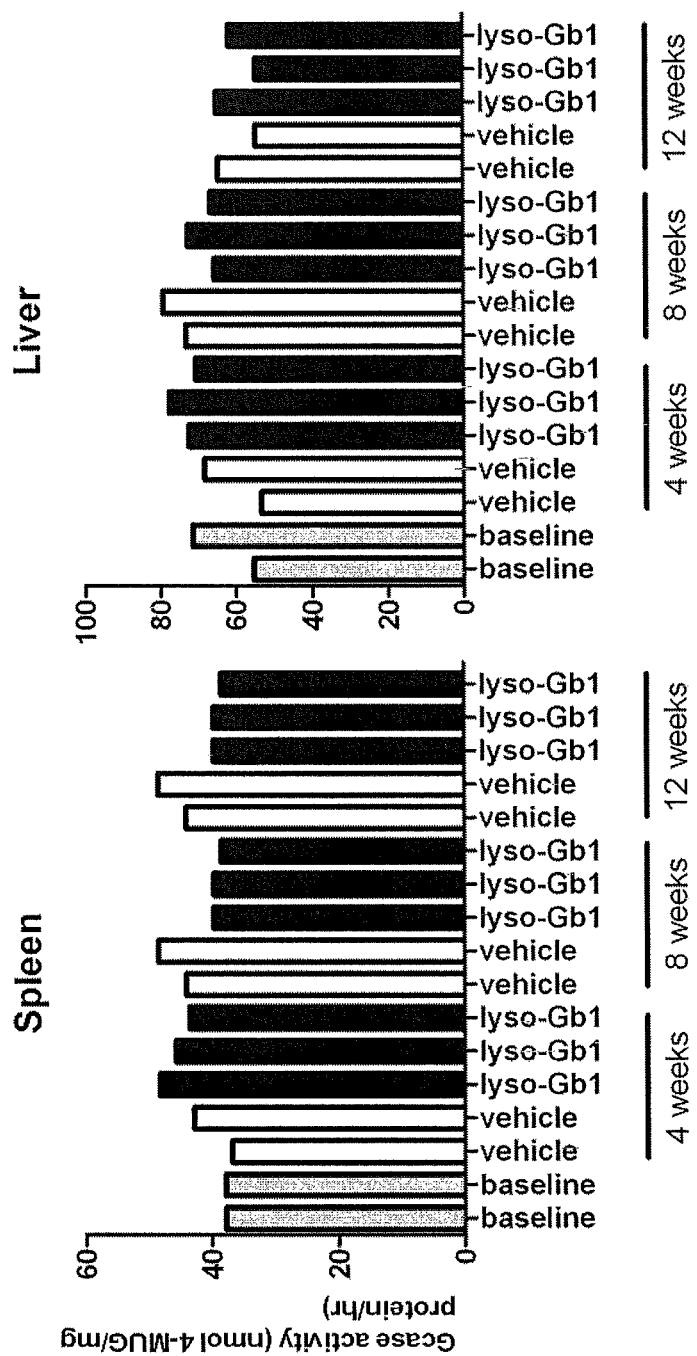

FIG. 7 represents bar diagrams showing GCase levels in spleen and liver lysates after 4, 8 and 12 weeks of after treatment initiation.

Figure 8:
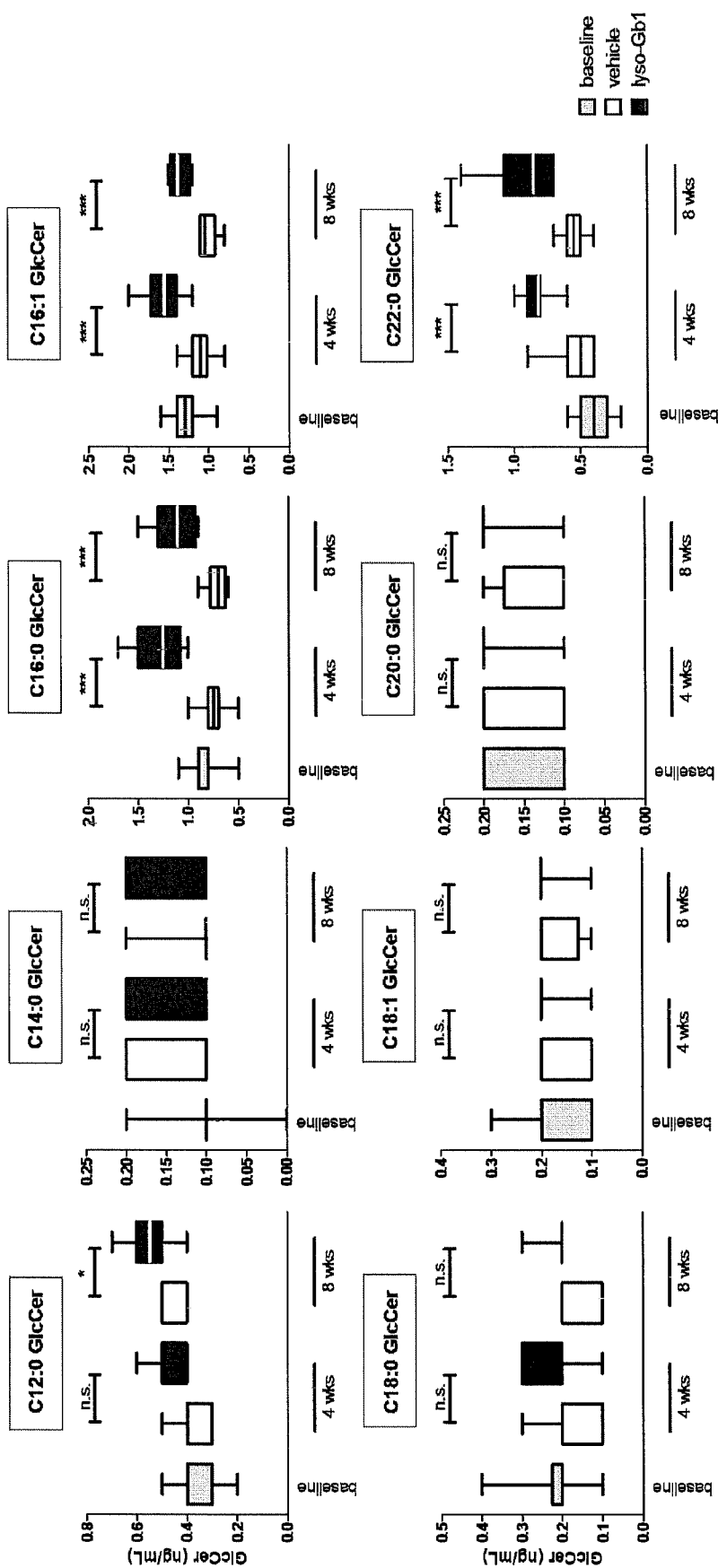

FIG. 8 are diagrams showing the level of different types of glucosylceramides in blood of mice treated with either lyso-Gb1 or vehicle alone, after 4 and 8 weeks.

As described supra, animal models of GD display a broad spectrum of neurological, hematological and visceral phenotypes based on the nature of the genetic defect. Both genetic and non-genetic (chemically-induced) GD mouse models provide informative insights into the disease pathology, often closely resembling the human phenotype (reviewed in Farfel-Becker et al., 2011, Dis Mod Mech 4:746-52). However, none of the disease models developed so far permit an isolated analysis of the effects attributable to sphingolipid storage alone.

As shown in the examples the inventors of the present inventions have developed an animal model that allows an isolated analysis of the effect of lyso-Gb1, independently from potential effects of GCase activity, GCase inactivity, glucosylceramide and/or accumulation of glucosylceramide.

EXAMPLES

Example 1: Materials and Methods

Animal Housing and Treatment

Animal experimental procedures were carried out at Pharmacelsus GmbH, Saarbrücken, Germany. Adult male C57BL/6JRj mice (10 weeks old, purchased from Janvier Labs, France) were housed in a temperature-controlled room (20-24° C.) and maintained in a 12 h light/12 h dark cycle. Food (Ssniff® R/M-H, 10 mm) and water were provided ad libitum.

All experimental procedures were approved by and conducted in accordance with the regulations of the local Animal Welfare authorities. The lyso-Gb1 stock solution was prepared in DMSO and propylene glycol at 37° C. with ultrasonic bath treatment for 10 min. Subcutaneous administration of lyso-Gb1 (Matreya LLC, USA) was achieved by the use of ALZET pumps implanted in the back of their necks and set to a flow rate of 2.64 µl/day in order to obtain a daily dosage of 10 mg lyso-Gb1/kg body weight. The pumps were loaded with the stock solution and primed prior to implantation according to the manufacturer's instructions.

Blood sampling was carried out using Li-heparine blood obtained from the lateral tail vein. At each sampling time point 2 aliquots of 20 µl were transferred to dried blood spot filter cards (Centogene AG, Rostock, Germany). After the last sampling time point the mice were sacrificed by inhalation of an overdose of isoflurane and organs were removed, frozen and collected for future examinations. Where applicable, organs were intersected. Half of the organ was immediately frozen in liquid nitrogen. The other half was formalin-fixed and paraffin-embedded for histologic analysis (Histalim, Montpellier, France).

Sample Preparation and Lyso-Gb1 Determination from Dried Blood Spots (Abbr. DBS)

3 punches of 3.2 mm in diameter were cut using a DBS puncher (Perkin Elmer LAS, Germany) and placed in a 2.2 ml round bottom tube (Eppendorf, Germany). 50 µl extraction solution (DMSO: water, 1:1) and 100 µl internal standard solution with the standard being dissolved in ethanol were added on top of the paper punches. Samples were mixed for 30 seconds and placed in an incubator (Heidolph, Schwabach, Germany) for 30 minutes at 37° C. under agitation at 700 rpm. After incubation, the tubes were sonicated for 1 minute at maximum power and then the liquid was transferred to a AcroPrep Filter Plate with PTFE membrane (PALL, Germany) placed on a 96 well V-shape bottom plate (VWR, Germany). The samples were filtrated by centrifugation for 5 minutes at 3,500 rpm in a Hermle Z300 plate centrifuge (Hermle Labortechnik, Germany) to remove any solid particles from the solution.

Preparation of Urine Samples for LC/MRM-MS Analysis

25 µL urine aliquots were added to 100 µL of internal standard and 250 µL ethanol. The samples were cooled to 4° C. for 1 h to precipitate the urine proteins, after which they were spun in a benchtop centrifuge for 3 minutes at 14,500 rpm. The volume of each sample was quantitatively transferred to a 96-well plate, and further processed as described above.

Organ Sample Preparation for Lyso-Gb1 Determination

After extraction from the animal, the organs were immediately deep-frozen in liquid nitrogen. The samples were lyophilized (Alpha 2-4 LSC, Christ, Osterode am Harz, GER) and powdered with mortar and pistil. Fractions of 2 to 5 mg powder were established in round bottom tubes. On top of the powder, 50 µl per mg powder extraction solution was added and the sample was incubated for 5 minutes at 37° C. under agitation. Subsequently, the samples were frozen in liquid nitrogen for 30 seconds and sonicated with boost function for 5 minutes. The incubation, freezing and sonication steps were repeated 6 times. At the end the mixtures were vortexed and aliquots of 25 µl suspension were used for the lyso-Gb1 determination. Each sample was supplemented with 100 µl Internal Standard (lyso-Gb2, 200 ng/ml) and 250 µl ethanol. The samples were cooled at 4° C. for 1 h to precipitate the membrane proteins and spun in a benchtop centrifuge for 3 minutes at 14.5 krpm. The volume of each sample was quantitatively transferred to a 96-well filter plate and further processed as described above.

LC/MRM-MS Measurements

LC-MRM-MS analyses of the lyso-Gb1 for both DBS and organ extracts were performed using a Waters Acquity UPLC (Waters, UK) coupled with an ABSciex 5500 TripleQuad mass spectrometer (ABSciex, Darmstadt, Germany). Chromatographic run was performed on a C8 column with pore size of 3 mM (ACE columns, Germany) using a flow rate of 0.9 ml/min preheated at 60° C. The 10 µl extract were injected on the column and the compounds were eluted using a linear gradient from 40% A (50 mM formic acid in water) to 100% B (50 mM formic acid in acetone:acetonitrile vol. 1:1). Upstream from UPLC a 3:1 flow splitter was added. The following MRM transitions were monitored: 624.3-282.2 for the internal standard (with DP of 30V, CE of 38 V and CXP of 10 V) and 462.3→282.2 for lyso-Gb1 (with DP of 28V, CE of 30 V and CXP of 10 V). MRM-MS analyses were performed in positive ion mode using the following parameters: CUR gas 40 psi, IS voltage 5.5 kV, CAD 8 psi, cone temperature 500° C., GS 1 45 psi, GS2 60 psi, EP 10 V. For all batches analyzed a standard curve was measured using 7 dilutions of lyso-Gb1 in ethanol (concentrations in ng/ml: 0; 5; 10; 50; 100; 200; 1000).

Blood Count

Mice were exsanguinated via the retrobulbar venous plexus under isoflurane anesthesia before being sacrificed by overdose inhalation. 200 µL EDTA samples of whole blood were drawn from each animal to analyze aspartate aminotransferase (AST/GOT), leukocyte count, erythrocyte count, hemoglobin (Hb), hematocrit (PCV=packed cell volume, Hct), mean cell volume (MCV), mean cell Hb (MCH), mean cell Hb concentration. (MCHC) and platelet count (PLT) (IDEXX Bioresearch, Ludwigsburg, Germany).

Cytokine Analysis

The ProcartaPlex® Multiplex Immunoassay (ebioscience, San Diego, Calif.) was carried out following the instructions of the provider. Differences between the animal groups were obtained using automated MAGPIX® analysis device software (Luminex, Austin, Tex.) including quality control criteria.

Western Blot

Livers and spleens were homogenized in RIPA buffer containing proteinase and phosphatase inhibitor (Roche, Mannheim, GER). Lysates were centrifuged at 15,000 g, 4° C. for 15 min to remove insoluble pellet, and supernatant was collected. Protein concentration was measured using Pierce BCA Protein Assay Kit (Thermo Fisher Scientific, Waltham, Mass.). Typically, 100 µs protein was loaded for electrophoresis on a 4%-15% precast Tris-glycine gradient gel (BioRad, Mannheim, GER). The protein was subsequently transferred to a nitrocellulose membrane by semidry transfer apparatus (BioRad, Munich, GER) for immunodetection analysis. The target proteins were detected by rat anti F4/80 (1:500, Biolegend, San Diego, Calif.), rat anti-CD68 [FA-11] (1:200 abcam, Cambridge, UK) mouse anti GAPDH (1:10,000, abcam, Cambridge, UK), each in TBST supplemented with 5% skim milk powder (Sigma Aldrich, Munich, GER). Fluorescent conjugate secondary antibodies were applied for the detection with a Li-Cor Odyssey imaging system (Bad Homburg, GER).

Histopathological Evaluation

After removal, organs were fixed in formalin for 24 h and transferred into 70% ethanol. To ensure a non-biased comparison the same parts of organs were analysed by HISTALIM (Montpellier, France). The samples were processed on the Peloris automaton (Leica, Wetzlar, Germany) according to the 4 h program validated for mouse organs. The samples were embedded in paraffin wax according to HISTALIM procedures. For the liver, spleen and femur samples, a section (3-5 µm thickness) was prepared and deposited preferentially on Superfrost+slide (to ensure tissue adhesion) to be stained according to a validated hematoxylin/eosin (H&E) protocol. All the slides were digitalised with the Nanozoomer scanner (Hamamatsu Photonics, Hamamatsu, Japan) in conditions bright field conditions, with the objective×20, without Z stack. Slides were examined by a senior histopathologist to assess the toxicological effects of lyso-Gb1 on the tested mice.

Immunohistochemistry

For immunohistochemistry 5 µm paraffin sections of the spleens of 8-week treated mice were subjected to rat anti-CD68 clone FA-11 (1:100, Bio-Rad Laboratories, Raleigh, N.C., USA) and rat anti-mouse F4/80 Cl:A3-1 (1:100, BioLegend, San Diego, Calif., USA). Sections were then deparaffinised, rehydrated and pre-treated in the microwaves in 0.1 M citrate buffer (5 min 850 W and 5 min 340 W) followed by consecutive incubation with 3% $H_2O_2$ in PBS to block endogenous peroxidases for 30 min, then 3% bovine serum albumin with 1.5% normal goat serum (NGS) in PBS for 1 h to block nonspecific epitopes. Subsequently, sections were exposed to the primary antibody in 3% NGS/PBS overnight at 4° C. Depending on the primary antibody and after washing in PBS, the sections were sequentially incubated for 1 h with the secondary anti-rat or anti-mouse IgG (1:200; Vector, Burlingame, Calif., USA), streptavidin-biotin-complex (ABC) reagent for 1 h (Vectastain-Elite; Vector, Burlingame, Calif., USA) and then finally visualised with 3,-3,-diaminobenzidine (DAB, Sigma, Munich, Germany), which was activated with $H_2O_2$. Sections were counterstained with hematoxylin, dehydrated, mounted with DePeX and coverslipped.

Data Analysis

Visualisation and statistical data evaluation were carried out using GraphPad Prism 5. Results are presented as median and range. The non-parametric two-tailed Mann-Whitney test was used to identify differences between treatment groups: hemoglobin, Hct and liver/spleen weight of control versus lyso-Gb1 treated mice at each indicated time point. Results were considered to be statistically significant for P values $<0.05*$, $<0.01$, $<0.005*$.

Glucocerebrosidase Enzyme Activity Measurement

Fresh-frozen liver and spleen samples were homogenized in pH 4.5 adjusted ice-cold potassium-phosphate buffer (100 µL/mg tissue) supplemented with 0.15% Triton X-100 and 0.125% sodium taurocholate. The tissue suspension was forced 10 times through a 22-gauge needle, equipped with a 2 mL syringe to release cell association. Thereafter, the suspension was subjected to 5 freeze/thaw cycles followed by centrifugation at 15,000×g for 15 minutes at 4° C. to obtain a cleared lysate. The protein concentration of the GCase containing extracts was measured and 9 µg whole protein was used for the enzymatic reaction using 2 mM final concentration 4-Methylumbelliferyl-ß-D-glucopyranoside (4-MUG) as substrate. The reaction was terminated by the addition of 0.2 mL of 1.0 M glycine buffer (pH 10.5). The free fluorophore 4-MU was determined in a microplate reader (Tecan, Männedorf, Switzerland).

Example 2: Lyso-Gb1 Levels Upon Continuous Subcutaneous Administration of Lyso-Gb1 to Mice Male C57BL/6JRj mice were equipped with sub-cutaneous osmotic mini-pumps in the back of their necks to achieve a long-term administration of lyso-Gb1 (12 weeks).

Recurrent DBS sampling was carried out in order to investigate the lyso-Gb1 level development in the organ system of the mice.

Figure 1A:
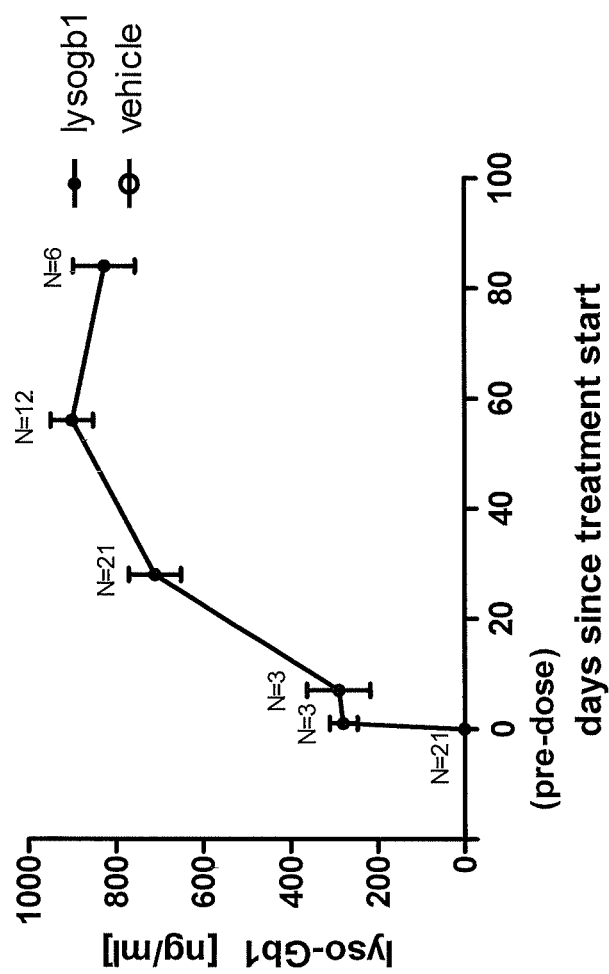
Figure 1B:
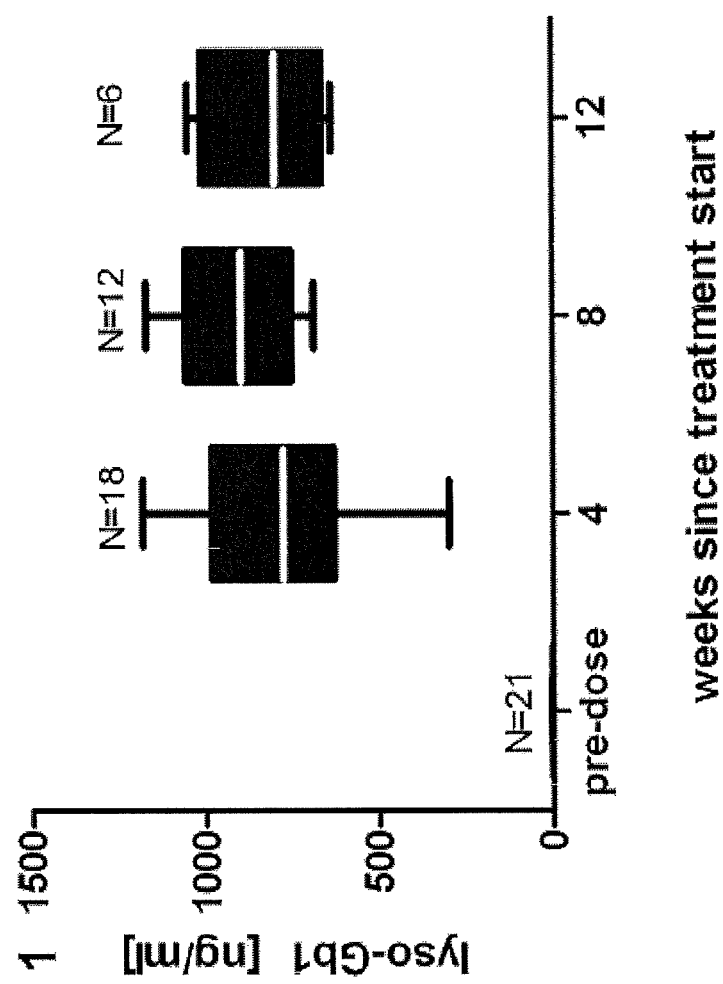

The result of the monitoring of blood lyso-Gb1 level in treated mice are shown in FIGS. 1 A and B.

As may be taken from FIGS. 1 A and B lyso-Gb1 levels were strongly elevated already 24 hrs after treatment start (data not shown). The lyso-Gb1 values observed after 24 hrs manifested throughout the treatment phase. After 4, 8 and 12 weeks lyso-Gb1 level ranged between 700-900 ng/ml, reflecting a more than 500-fold increase compared to the vehicle-treated mice. Vehicle-treated (or pre-dose) animals had lower, but detectable lyso-Gb1 values around 1.2-1.5 ng/ml blood (FIGS. 1 A and B).

After 4 weeks from treatment start the organs of the mice were subjected to lyso-Gb1 analysis. The results are shown in FIG. 2A.

Figure 2A:
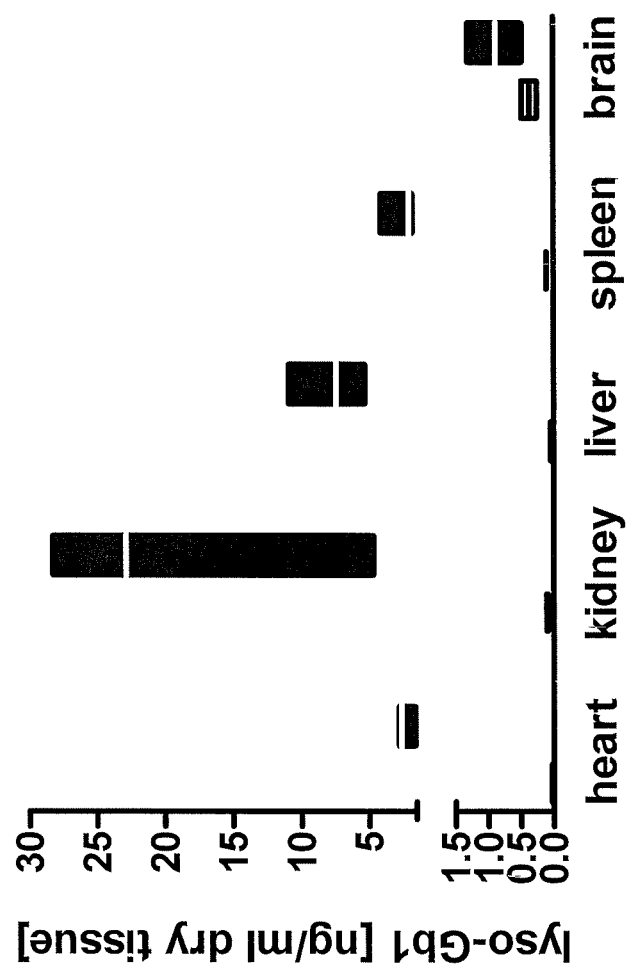
Figure 2B:
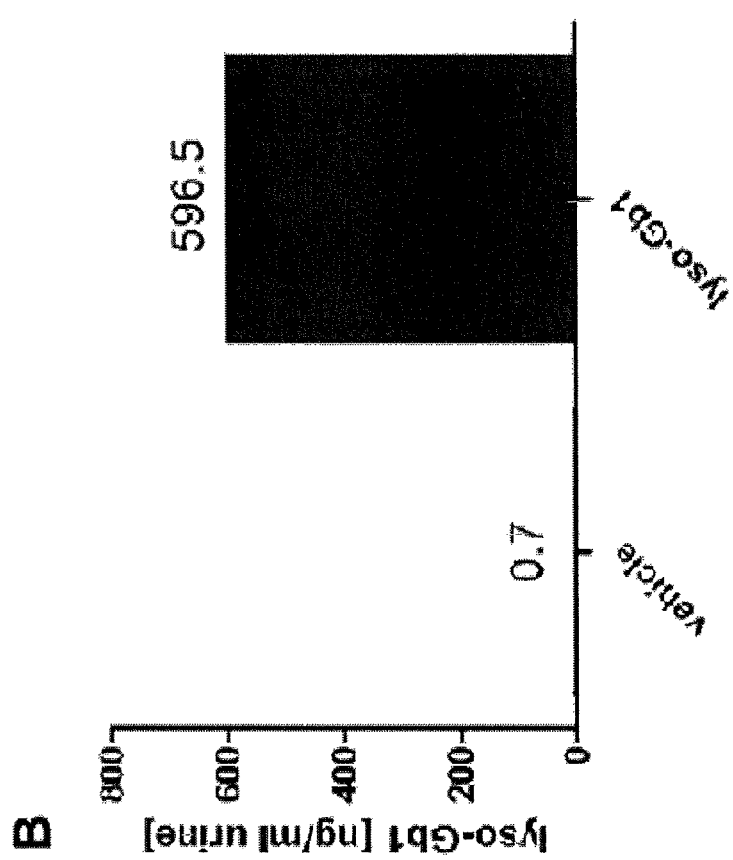

As may be taken from FIG. 2A, after 4 weeks from treatment (10 mg*kg$^{-1}$*day$^{-1}$) start the heart, kidney, liver, spleen and brain were analysed for lyso-Gb1 accumulation. All peripheral organs of treated mice showed strongly elevated levels of lyso-Gb1 compared to control animals. Highest levels of lyso-Gb1 were detected in the kidney which indicates a predominant urinary elimination of the water-soluble lyso-Gb1. This was verified by urinary levels of lyso-Gb1 (FIG. 2B). A dramatic increase of lyso-Gb1 was also observed in all other peripheral organs whereas the fold change was more pronounced in liver and less pronounced in spleen. A small, 2-fold increase of brain lyso-Gb1 was attributed to carryover of blood in the tissue capillaries, which had not been cleared by perfusion prior to analysis.

Figure 3:
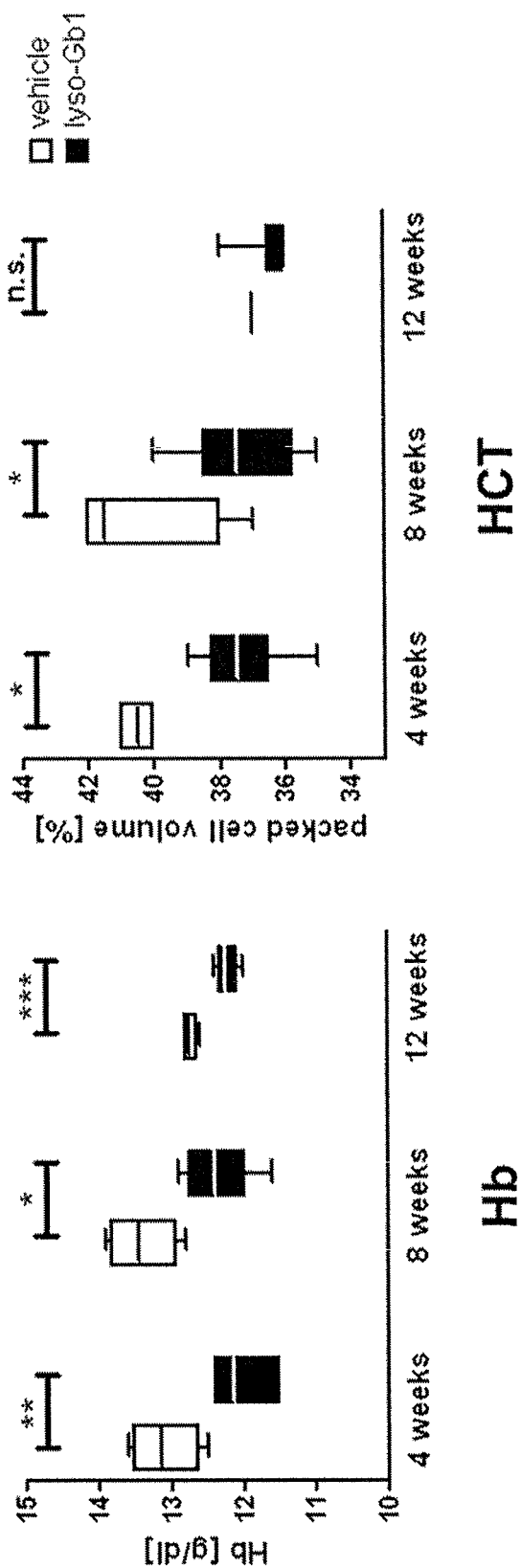

Example 3: Analysis for Systemic Damage of Lyso-Gb1 Treated Mice 3.1 It was tested whether the high lyso-Gb1 levels caused systemic damage to the animals. Such systemic damage was assessed by blood count analysis. The results are shown in FIG. 3.

As evident from FIG. 3, left diagram, Hb values were slightly reduced and laid 2× SD below the baseline value at each time point indicating a mild anaemia as defined by Raabe et al. (Raabe et al., 2011, supra). The control groups at all time points were compared and no statistical difference was found between them More specifically, the animal displaced lowered Hct and Hct values differed at 4 and 8 weeks after treatment initiation (FIG. 3, right diagram). The depression of control values at week 12 was significant and could be a consequence of the vehicle (50% DMSO/50% propylene glycol) treatment, because propylene glycol (ADDENDUM for PROPYLENE GLYCOL Supplement to the 1997 Toxicological Profile for Propylene Glycol; https://www.atsdr.cdc.gov/toxprofiles/propylene_glycol_addendum.pdf) has been demonstrated to be a hematologically effective compound. The low infusion volume, and reported tolerability of the compound in markedly higher doses (Thackaberry et al., 2010, Toxicol Sci, 117: 485-492), makes this unlikely. More important, however, is the fact that there is no further progression in Hct reduction in the lyso-Gb1 treated animals.

It is to be noted that no thrombocytopenia or abnormalities in white blood cells (WBC) were observed. Tables S1A and S1B(FIG. 6) summarize all relevant parameters compiled in this study.

3.2 As anemia is a frequent result of enlarged spleen, another hallmark of Gaucher disease, an organ weight analysis, a Western blot analysis and size and color analysis of the spleen was carried out. The results thereof are shown in FIG. 4A, FIG. 4B and FIG. 4C.

Figure 4:
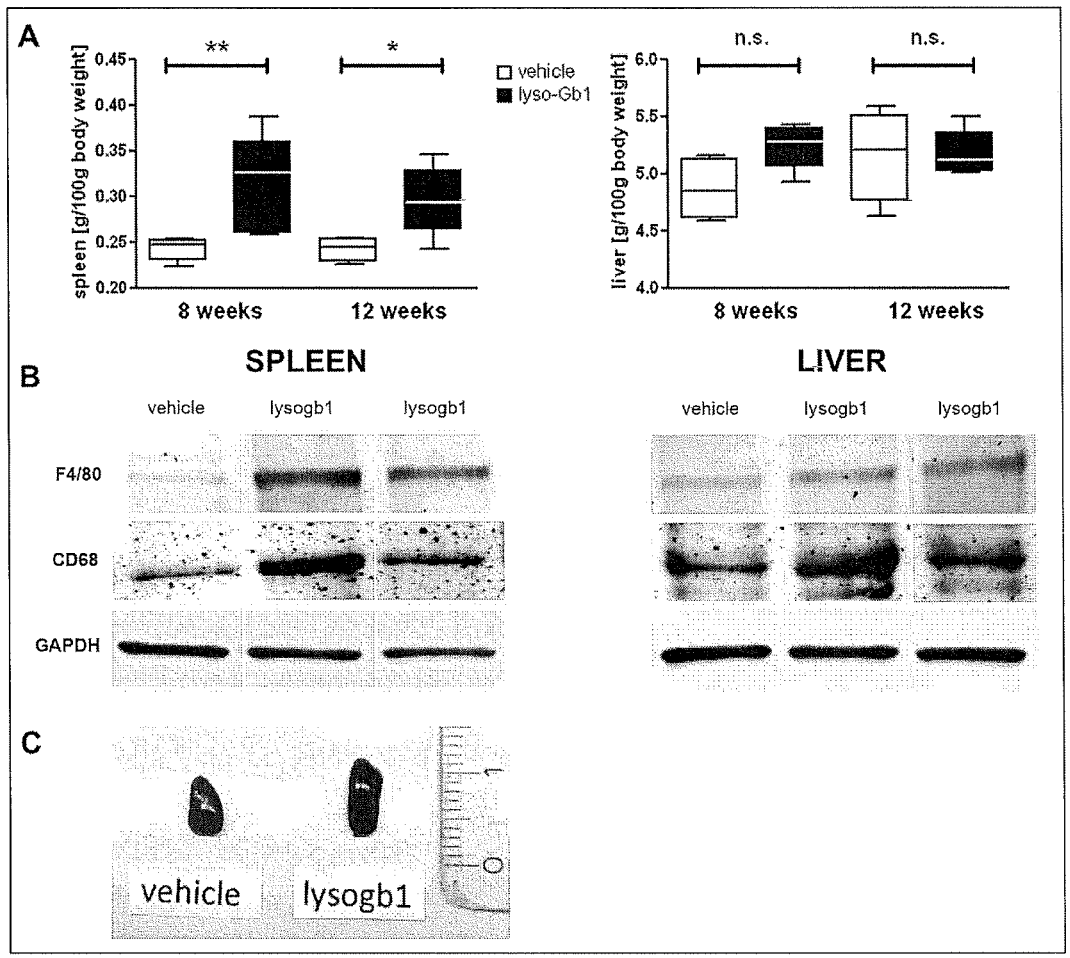
FIG. 4B is a panel of two diagrams illustrating the result of a Western blot analysis of inflammatory tissue markers F4/80 and CD68 in spleen and liver, whereas a pronounced increase in spleen levels for F4/80 and CD68 was observed in the lyso-Gb1 treated mice after 8 and A similar increase was noted in the livers of the same animals.
FIG. 4C is a photograph showing half of a spleen from a control and lyso-Gb1 treated animal, whereas The organ samples illustrate the change in size and a distinctive color.

FIG. 4A summarizes the results obtained from organ weight analysis of lyso-Gb1 treated C57BL/6JRj mice. As evident from FIG. 4A, the spleens of the treated mice were enlarged after 8 and 12 weeks from treatment initiation compared to the control organs. Liver weight was not statistically distinct from control animals and the animals had thus no hepatomegaly.

In order to investigate the molecular changes of both spleen and liver in terms of tissue inflammation macrophagic marker proteins F4/80 and CD68 were analysed. FIG. 4B shows the result of a Western blot analysis of said inflammatory tissue markers F4/80 and CD68. Consistent with organ weights, the levels of both proteins were elevated in the spleen, whereas only mild changes were observed in the liver.

Finally, visual inspection of half of a spleen from a control and a lyso-Gb1 treated animal was performed. The organ samples illustrate the change in size and a distinct colour appearance (see FIG. 4C).

A general histological stain of the spleens (also liver and femur) for all animals using H&E did not reveal significant abnormalities between vehicle and lyso-Gb1 treated organs (data not shown), but immunohistochemical analysis using specific antibodies confirmed the Western blot results. In detail, H&E-stained sections of spleen showed a similar morphology in white and red pulp in both vehicle and lyso-Gb1 treated mice (FIG. 5A, B). Immunohistochemical data revealed a strong increase in CD68-immunoreactivity in lyso-Gb1 treated mice, when compared to vehicle controls (FIG. 5C, D). In particular, accumulation of CD68-positive cells was seen near the capsule (FIG. 5E, F). Also, F4/80 immunoreactivity was increased in lyso-Gb1 treated mice compared to vehicle controls (FIG. 5G, H). Higher magnification showed that the qualitative staining intensity of F4/80-positive cells was weak to medium compared to that of CD68 positive cells in the spleen of lyso-Gb1 treated mice (FIG. 5E, F to I, K).

Lyso-Gb1 is a potential substrate of GCase, which poses the question whether the treatment can influence proper enzyme function in the animals as assessed before (Vacaro et al., 1985, Eur J Biochem 14: 351-21). Enzyme measurements in spleen and liver lysates showed normal ex vivo activity (FIG. 7) providing evidence that lyso-Gb1 did not significantly influence wild type GCase in the mice. This discovery is further supported by the fact that glucosylceramide levels are only moderately affected (FIG. 8).

Example 4: Interpretation of the Results of Examples 2 and 3

Ten weeks old C57BL/6JRj mice were subcutaneously treated with high doses (10 mg*kg−1*day−1) of lyso-Gb1 for a period of up to 84 days (12 weeks).

The mice developed a phenotype in blood and spleen comparable to a mild form of Gaucher disease, whereby phenotype resembles the phenotype observed in genetic mouse models of Gaucher disease type 1.

The treatment led to an accumulation of lyso-Gb1 in all major tissues and a robust blood concentration of >500 ng/ml blood 4 weeks after begin of treatment, despite the presence of normal GCase. One explanation for this could be the lower capacity of GCase to hydrolyse lyso-Gb1 in comparison to Glucosylceramide (Vacaro et al, supra). Typically, Gaucher patient plasma lyso-Gb1 levels range from 50-250 ng/ml prior to enzyme replacement therapy (abbr.

ERT) (Rolfs et al., PLoS One. 8(11): e79732) suggesting that the obtained concentration in the mouse circulation was comparable, because, at least in humans, lyso-Gb1 blood level exceeds the plasma values by a factor of >2 (unpublished data). Since it was discovered that lyso-Gb1 levels are associated with disease severity (Dekker et al., 2011, supra; Rolfs et al., 2013, supra) it can therefore be expected that the observed lyso-Gb1 concentration, if initially causative to GD symptom onset, was high enough to produce a similar phenotype in mice as in patients, most typically hepatosplenomegaly, anemia and bone disease.

Glucosylceramide and glucosylsphingosine are believed to be responsible for macrophagic organ infiltration and, consequently, the development of organomegalies. Therefore, organ weight analysis of the treated animals was performed. The gain in spleen weight was consistent with the dramatic increase in lyso-Gb1 in this organ and the observed elevation of CD68 and F4/80 antigen confirmed by Western blot and immohistochemistry. This could suggest either an early stage or chronic inflammation within this tissue due to an increased number of immune cells, likely macrophages (Boven et al., 2004, Am J Clin Pathol 122: 359-369; Kinoshita et al., 2010, J Hepatol, 53: 903-910), despite the variation in cell populations positively stained for CD68 and F4/80. In contrast, heart, lung and kidney appeared to be normal in size. Liver weight was slightly elevated at 8 weeks of treatment, albeit not statistically significantly so, and histological examination of liver sections suggested no pathophysiological condition. However, corresponding hepatic CD68 and F4/80 levels appeared mildly elevated, and we marked enlargement of the liver was observed in a subsequent experiment where lyso-Gb1 treatment was started earlier (P20) (data not shown). This experiment also confirmed the spleen enlargement and decreased Hb and Hct originally reported in genetic non-neuronopathic GD mice (Enquist et al., 2006, Proc Natl Acad Sci USA, 103: 13819-13824).

No further progression in phenotype severity was observed after 8 weeks of treatment with regards to organ weight and blood parameters; this suggests a physiological adaptation by the mice, or perhaps the absence of critical lyso-Gb1 concentrations at crucial target locations. Furthermore, the mice displayed no obvious health problems or functional constraints and did not lose weight throughout the experimental phase. This finding is contrary to the situation in a genetic mouse model with no apparent CNS involvement which demonstrated weight loss of 15% compared to healthy mice at 50 days of age, but no further progressive decline (Mizukami et al., 2002, J Clin Invest. 109(9):1215-21). The mice introduced by Mizukami et al. showed minimal glucosylceramide storage and the absence of classic Gaucher tissue infiltration. However, their mice did display multisystemic inflammation reflecting elevated hepatic TNF-α and IL-1β expression, highlighting that rather inflammation is the key feature of GD that might not necessarily be typified by the presence of Gaucher cells. Our lyso-Gb1-treated mice showed slight elevation of TNF-α and IL-1β in the blood, as observed by ProcartaPlex® Multiplex Immunoassay, possibly indicating B-cell proliferation. However, we did not find significant upregulation of most investigated cytokines (FIG. 6).

Late start of attendance of the mice (10 week old animals) is a likely explanation why the observed physiological changes in the peripheral tissues do not show the entire symptom spectrum of the disease. Earlier reports substantiated an elevation of lyso-Gb1 in the mouse body in embryonic phase (Orvisky et al., 2000, Pediatr Res. 48(2): 233-7). However, this finding concerned a neuronopathic Gaucher mouse model. To date, there is no pre-natal study on lyso-Gb1 in a non-neuronopathic mouse model, but it is reasonable to assume that lyso-Gb1 is also elevated during early developmental stages since it was found to be elevated in tissue of very young individuals (Orvisky et al., 2002, Mol Genet Metab. 76(4):262-70).

In contrast to the GD patients and also the genetic mouse model of GD examined by Orvisky and colleagues (Orvisky et al., 2000, supra), where highest lyso-Gb1 levels were observed in the spleen, we observed a different distribution, with the highest lyso-Gb1 levels measured in the kidney and liver. The reported finding from Orvisky and colleagues would indicate that lyso-Gb1 in GD originates from intrasplenic macrophage sources, whereas in our model, kidney and liver, not surprisingly, appeared to take up more of the subcutaneously administered lyso-Gb1. The negligible increase in lyso-Gb1 levels in the animal brain indicates that lyso-Gb1 is not able to cross the blood brain barrier. No CNS measurements were performed as the animals displayed no behavioral abnormalities, and the basal lyso-Gb1 level in the brain was higher than in peripheral organs. This suggests better tolerance for lyso-Gb1 in the CNS.

Most known GD models have the disadvantage of rapid decline, which hampers the close examination of disease progression. Most GD patients carry the N370S allele, which is associated with a late disease onset, mild symptoms and slow disease progression. It was shown that certain, primarily homozygous, patients remain asymptomatic throughout life (Balwani et al., 2010, Arch Intern Med, 170: 1463-1469). Investigating the relationship between the pathophysiology of GD and the phenotype in the lyso-Gb1 treated animals can be used to gain a better understanding of common and milder GD alleles. The N370S mutation can, however, also be found in patients with an early disease onset (Balwani et al, supra). Recent findings strongly suggest a critical role for the genetic background (Klein et al., 2016, Cell Rep, 16: 2546-53) in the phenotypic severity of GD animal models and patients. It can also be speculated that differences in the metabolic pathways of the animals contribute to disease development. Consequently, the lyso-Gb1 treatment of a single inbred mouse strain does not adequately reflect the complex spectrum of phenotypes manifested inhuman GD.

The present mouse model could be used to investigate the efficacy of lyso-Gb1 neutralizing agents (e.g. antibodies and aptamers) as a potential drug therapy for GD. Engineering of monoclonal antibodies to target hematological diseases, such as specific cancers, is becoming a standard therapy. Strategies to inactivate bioactive lipids by antibodies and aptamers have already been adopted (Sabbadini R A.; British Journal of Pharmacology. 2011; 162(6):1225-1238; WO 2011/15341; Purschke et al., Biochem J. 2014 Aug. 15; 462(1):153-62; international patent application WO 2011/131371). The analysis of anti-inflammatory drug effects on the visceral signs of GD could help to reveal whether the observed inflammatory tissue reaction is sufficient to protect the mice from emerging disease signs, explaining their unaltered overall health status.

Example 5: Lyso-Gb1 in Parkinson's Disease

Patients suffering from Parkinson's disease having a mutation in GBA (glucocerebrosidase) show in increased level of lyso-Gb1 compared to patients suffering from Parkinson's disease without GBA mutation. The lyso-Gb1 level is always below 12 ng/ml which is the critical threshold for patients suffering from Gaucher disease, but is still increased (7.9 ng/ml vs. 2.8 ng/ml). The lyso-Gb1 level of these patients suffering from Parkinson's disease is also increased compared to patients being carrier for Gaucher disease, but not being carrier for Parkinson's disease.

These data are supportive that lyso-Gb1 is involved in the pathophysiology of Parkinson's disease caused by mutations of GBA.

The features of the present invention disclosed in the specification, the claims, the sequence listing and/or the drawings may both separately and in any combination thereof be material for realizing the invention in various forms thereof.

The invention claimed is:

1. A method of using lyso-Gb 1 as a druggable target in the development of a drug antagonizing lyso-Gb 1 by physical interaction for the treatment and/or prevention of Gaucher disease, wherein the method comprises:
   determining in vitro whether a drug candidate binds to lyso-Gb 1 present outside of a cell, tissue or organ,
   determining in vivo whether the drug candidate is antagonizing the action of lyso-Gb 1 resulting in ameliorating at least one peripheral symptom of the disease, wherein the at least one symptom of the disease is selected from the group consisting of visceral enlargement of the spleen, mild anemia and inflammatory tissue response in the spleen; wherein the drug candidate is a drug for the treatment and/or prevention of Gaucher disease if the at least one symptom is ameliorated,
   and wherein lyso-Gb 1 is of formula (I)

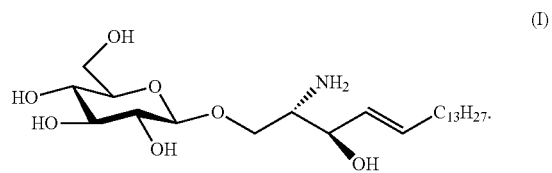

2. The method of claim 1 further comprising determining the binding affinity of the drug candidate to lyso-Gb 1.

3. The method of claim 1, wherein the drug candidate is identified in a screening process from a library of compounds, wherein the screening process comprises providing a library of compounds and identifying from the library of compounds one or more drug candidates capable of binding to lyso-Gb 1.

4. The method of claim 1, wherein the inflammatory tissue response in the spleen is indicated by an increased level of tissue inflammation macrophagic marker proteins F4/80 and CD68.

* * * * *

UNITED STATES PATENT AND TRADEMARK OFFICE
CERTIFICATE OF CORRECTION

PATENT NO. : 11,097,016 B2  
APPLICATION NO. : 16/312090  
DATED : August 24, 2021  
INVENTOR(S) : Cozma et al.

Page 1 of 1

It is certified that error appears in the above-identified patent and that said Letters Patent is hereby corrected as shown below:

On the Title Page

Item (30) Foreign Data:  
Please correct "Jul. 1, 2016 (EP) 16001474" to read -- Jul. 1, 2016 (EP) 16001474.2 --

Item (56) References Cited, Other Publications, top right column, Line 1, John Flanagan cite:  
Please correct "of gluposylsphingosine" to read -- of glucosylsphingosine --

In the Specification

Column 15, Embodiment 133, Line 28:  
Please correct "embodiments 130 to 1323," to read -- embodiments 130 to 132, --

Signed and Sealed this  
Twenty-ninth Day of March, 2022

Drew Hirshfeld  
*Performing the Functions and Duties of the*  
*Under Secretary of Commerce for Intellectual Property and*  
*Director of the United States Patent and Trademark Office*